United States Patent
O'Donnell

(10) Patent No.: US 6,221,642 B1
(45) Date of Patent: Apr. 24, 2001

(54) **PROCESS FOR RECONSTITUTING THE POLYMERASE III* AND OTHER SUBASSEMBLIES OF E. COLI DNA POLYMERASE III HOLOENZYME FROM PEPTIDE SUBUNITS**

(75) Inventor: Michael E. O'Donnell, Hastings-on-Hudson, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 0 days.

(21) Appl. No.: 09/282,917

(22) Filed: Mar. 31, 1999

Related U.S. Application Data

(62) Division of application No. 08/696,651, filed on Aug. 14, 1996, now abandoned, which is a continuation of application No. 08/298,945, filed on Aug. 31, 1994, now Pat. No. 5,583,026.

(51) Int. Cl.$^7$ .............................. C12N 9/12; C12N 9/10
(52) U.S. Cl. ........................................ 435/194; 435/193
(58) Field of Search ...................................... 435/193, 194

(56) References Cited

U.S. PATENT DOCUMENTS 5,583,026 * 12/1996 O'Donnell ........................... 435/194

FOREIGN PATENT DOCUMENTS

WO 93/15115    8/1993 (WO).

OTHER PUBLICATIONS

Tsuchihashi et al., J. Biol. Chem., 264(30), "ATP Interactions of the tau and gamma Subunits of DNA Polymerase III Holoenzyme of *Escherichia coli*", pp. 17790–17795, Oct. 1989.*

Onrust et al., J. Biol. Chem., 268(16), "DNA Polymerase III Accessory Proteins", pp. 11766–11772, Jun. 1993.*

Dallmann et al., J. Biol. Chem., 270(49), "DnaX Complex of *Escherichia coli* DNA Polymerase III Holoenzyme", pp. 29555–29562, Dec. 1995.*

Dallmann et al., J. Biol. Chem., 270(49), "DnaX Complex of *Escherichia coli* DNA Polymerase III Holoenzyme", pp. 29563–29569, Dec. 1995.*

Olson et al., J. Biol. Chem., 270(49), "DnaX Complex of *Escherichia coli* DNA Polymerase III Holoenzyme", pp. 29570–29577, Dec. 1995.*

Pritchard et al., J. Biol. Chem., 271(17), "In vivo Assembly of the tau–Complex of the DNA Polymerase III Holoeznyme Expressed from a Five–Gene Artificial Operon", pp. 10291–10298, Apr. 1996.*

Onrust, R., O'Donnell, M., "DNA polymerase III accessory proteins. II. Characterization of $\delta$ and $\delta N$," *J. Biol. Chem.*, 268:11766–72 (1993).

Dong, A., Onrust, R., Skangalis, M., and O'Donnell, M., "DNA polymerase III accessory proteins. I. holA and holB encoding $\delta$ and $\delta N$," *J. Biol. Chem.*, 268:11758–65 (1993).

(List continued on next page.)

*Primary Examiner*—Jon P. Weber
(74) *Attorney, Agent, or Firm*—Nixon Peabody LLP

(57) ABSTRACT

The process of the invention provides for the reconstitution of the polymerase III* subassembly, Pol III*, of *E. coli* DNA polymerase III holoenzyme from substantially pure peptide subunits. In the first of two general schemes in which the subunits are added in a specified order, $\gamma$ and $\tau$ are premixed before addition of $\delta$ and $\delta'$. In the second general scheme, $\delta'$ is first assembled onto $\gamma$ (or $\tau$); then the excess $\delta'$ is removed before adding $\tau$ (or $\gamma$), following which $\delta$ is added. Reconstituted Pol III* had the same subunit composition as purified natural Pol III*, as well as similar activity. Other smaller subassemblies of the polymerase III holoenzyme may also be reconstituted by the process of the invention.

7 Claims, 14 Drawing Sheets

OTHER PUBLICATIONS

Xiao, H., Crombie, R., Dong, Z., Onrust, R., and O'Donnell, M., "DNA polymerase III accessory proteins. III. holC and holD encoding $\chi$ and $\psi$," *J. Biol. Chem.*, 268:11779–84 (1993).

Xiao, H., Dong, Z., and O'Donnell, M., 1993, "DNA polymerase III accessory proteins. IV. Characterization of $\chi$ and $\psi$," *J. Biol. Chem.*, 268:11773–78 (1993).

Studwell–Vaughan, P.S. and O'Donnell, M., "DNA polymerase III accessory proteins. V. $\theta$ encoded by holE," *J. Biol. Chem.*, 268:11785–91 (1993).

Carter, J.R., Franden, M.A., Aebersold, R., and McHenry, C.S., "Molecular cloning, sequencing, and overepxression of the structural gene encoding the $\delta$ subunit of *E. coli* DNA polymerase III holoenzyme," *J. Bacteriol.*, 174:7013–25 (1993).

Carter, J.R., Franden, M.A., Aebersold, R., and McHenry, C.S., "Identification, isolation, and characterization of the structural gene encoding the $\delta$N subunit of *E. coli* DNA polymerase III holoenzyme," *J. Bacteriol*, 175:3812–22 (1993).

Carter, J.R., Franden, M.A., Aebersold, R., Kim, D.R., and McHenry, C.S., "Isolation, sequencing and overexpression of the gene encoding the $\theta$ subunit of DNA polymerase III holoenzyme," *Nuc. Acids Res.*, 21:3281–86 (1993).

Carter, J.R., Franden, M.A., Aebersold, R., and McHenry, C.S., "Identification, isolation, and overepxression of the gene encoding the $\psi$ subunit of DNA polymerase III holoenzyme," *J. Bacteriol.*, 175:5604–10 (1993).

Carter, J.R., Franden, M.A., Lippincott, J.A., and McHenry, C.S., "Identification, molecular cloning and characterization of the gene encoding the $\chi$ subunit of DNA polymerase III holoenzyme of *E. coli*," *Mol. Gen. Genet.*, 241:399–408 (1993).

Tomasiewicz, H.G. and McHenry, C.S., "Sequence Analysis of the *Escherichia coli* dnaE Gene," *J. Bacteriol.* 169:5735–44 (1987).

Ohmori, H., Kimura, M., Nagata, T., and Sakakibara, Y., "Structural analysis of the dnaA and dnaN genes of *Escherichia coli*," *Gene*, 28:159–170 (1984).

Flower, A.M. and McHenry, C.S., "The adjacent dnaZ and dnaX genes of *Escherichia coli* are contained within one continuous open reading frame," *Nuc. Acids Res.*, 14:8091–8101 (1986).

Yin, K., Blinkowa, A., and Walker, J.R., "Nucleotide sequence of the *Escherichia coli* replication gene dnaZX," ibid., pp 6541–6549.

Maki, J., Horiuchi, T., and Sekuguchi, M., "Structure and expression of the dnaQ mutator and the RNase H genes of *Escherichia coli*: Overlap of the promoter regions," *Proc. Natl Acad. Sci. USA*, 80:7137–41 (1983).

Lasken, R.S. and Kornberg, A., "The $\beta$ Subunit Dissociates Readily from the *Escherichia coli* DNA Polymerase III Holoenzyme," *J. Biol. Chem.*, 262:1720–24 (1987).

Studwell–Vaughan, P.S. and O'Donnell, M., "Constitution of the Twin Polymerase of DNA Polymerase III Holoenzyme," *J. Biol. Chem.*, 266(29):19833–41 (1991).

Maki, H., Maki, S., and Kornberg, A., "DNA Polymerase III Holoenzyme of *Escherichia coli*. IV The Holoenzyme is an Asymmetric Dimer with Twin Active Sites," *J. Biol. Chem.*, 263:6570–78 (1988).

Maki, S. and Kornberg, A., "DNA Polymerase III Holoenzyme of *Escherichia Coli*. II. A Novel Complex Including the $\gamma$ Subunit Essential for Processive Synthesis," *J. Biol. Chem.*, vol. 263(14):6555–60 (1988).

O'Donnell, M. and Studwell, P.S., "Total Reconstitution of DNA Polymerase III Holoenzyme Reveals Dual Accessory Protein Clamps," *J. Biol. Chem.*, 265(2):1179–87 (1990).

Blinkova, A., Hervas, C., Stukenberg, P.T., Onrust, R., O'Donnell, M.E., and Walker, J.R., "The *Escherichia coli* DNA Polymerase III Holoenzyme Contains Both Products of the dnaX Gene, $\tau$ and $\gamma$, but only $\tau$ is Essential," *J. Bacteriol.*, 175:6018–27 (1993).

Studwell, P.S. and O'Donnell, M., "Processive Replication is Contingent on the Exonuclease Subunit of DNA Polymerase III Holoenzyme," *J. Biol. Chem.*, 265:1171–78 (1990).

Kong, X., Onrust, R., O'Donnell, M., and Kuriyan, J., "Three–Dimensional Structure of the $\beta$ Subunit of *E. coli* DNA Polymerase III Holoenzyme: A Sliding DNA Clamp," *Cell*, 69:425–37 (1992).

Fradkin, et al., "Prereplicative Complexes of Components of DNA Polymerase III Holoenzyme of *Escherichia coli*," *J. Biol. Chem.* 267(15):10316–22 (1992).

Wu, et al., "Coordinated Leading– and Lagging–Strand Synthesis at the *Escherichia coli* DNA Replication Fork," *J. Biol. Chem.* 267(6):4064–73 (1992).

Reems, et al., "*Escherichia coli* DNA Polymerase III Holoenzyme Footprints Three Helical Turns of Its Primer," *J. Biol. Chem.* 269(52):33091–96 (1994).

Burgers, et al., "ATP Activation of DNA Polymerase III Holoenzyme of *Escherichia coli*," *J. Biol. Chem.* 257(19):11468–73 (1982).

Wu, et al., "Coordinated Leading– and Lagging–Strand Synthesis at the *Escherichia coli* DNA Replication Fork," *J. Biol. Chem.* 267(6):4030–44 (1992).

Zechner, et al., "Coordinated Leading– and Lagging–Strand Synthesis at the *Escherichia coli* DNA Replication Fork," *J. Biol. Chem.* 267(6):4045–53, 4054–63 (1992).

Wu, et al., "Coordinating Leading– and Lagging–Strand Synthesis at the *Escherichia coli* DNA Replication Fork," *J. Biol. Chem.* 267(6):4074–83 (1992).

Onrust, et al., "Analysis of the ATPase Subassembly Which Initiates Processive DNA Synthesis by DNA Polymerase III Holoenzyme," *J. Biol. Chem.* 266(32):21681–86 (1991).

McHenry, "DNA Polymerase III Holoenzyme," *J. Biol. Chem.* 266(29):19127–30 (1991).

Maki, et al., "DNA Polymerase III Holoenzyme of *Escherichia coli*," *J. Biol. Chem.* 263(14):6547–54, 6561–69 (1991).

Maki, et al., "The Polymerase Subunit of DNA Polymerase III of *Escherichia coli*," *J. Biol. Chem.* 260(24):12982–86, 12987–92 (1985).

McHenry, "DNA Polymerase III Holoenzyme of *Escherichia coli*," *Ann. Rev. Biochem.* 57:519–50 (1988).

\* cited by examiner

PROCESS FOR RECONSTITUTING THE POLYMERASE III* AND OTHER SUBASSEMBLIES OF E. COLI DNA POLYMERASE III HOLOENZYME FROM PEPTIDE SUBUNITS

This application is a division of U.S. patent application Ser. No. 08/696,651, filed on Aug. 14, 1996, now abandoned, which is a continuation of U.S. patent application Ser. No. 08/298,945, filed Aug. 31, 1994, now U.S. Pat. No. 5,583,026, which are hereby incorporated by reference.

This work was supported by grants from the National Institute of Health (GM38839) and the National Science Foundation MCB-9303921).

FIELD OF THE INVENTION

This invention relates to a process for reconstituting the polymerase III* and other subassemblies of E. coli DNA polymerase III holoenzyme from peptide subunits.

BACKGROUND OF THE INVENTION

The disclosures of all patents and publications cited in the specification are incorporated herein by reference.

DNA polymerase III holoenzyme ("Pol III") was first purified and determined to be the principal replicase of the E. coli chromosome by Kornberg (A. Kornberg, 1982 Supplement to DNA Replication, Freeman Publications, San Francisco, pp 122–125). The E. coli replicase is composed of a DNA polymerase subunit accompanied by multiple accessory proteins and contains at least ten subunits in all (McHenry and Kornberg, 1977, J. Biol. Chem., vol. 252, pp 6478–6484; Maki and Kornberg, 1988, J. Biol. Chem., vol. 263, pp 6551–6559). It has been proposed that chromosomal replicases may contain a dimeric polymerase in order to replicate both the leading and lagging DNA stands concurrently (Sinha et al., 1980, J. Biol. Chem., vol. 225, pp 4290–4303).

One of the features of Pol III which distinguishes it as a chromosomal replicase is its use of ATP to form a tight, gel filterable "initiation complex" on primed DNA (Burgers and Kornberg, 1982, J. Biol. Chem., vol. 257, pp 11468–11473). The holoenzyme initiation complex completely replicates a uniquely primed bacteriophage single-strand DNA ("ssDNA") genome coated with the ssDNA binding protein ("SSB"), at a speed of at least 500 nucleotides per second at 30° C. without dissociating from an 8.6 kb circular DNA even once (Fay et al., 1981, J. Biol. Chem., vol. 256, pp 976–983; O'Donnell and Kornberg, 1985, J. Biol. Chem., vol. 260, pp 12884–12889; Mok and Marians, 1987, J Biol. Chem., vol. 262, pp 16644–16654). This remarkable processivity, i.e., the high number of nucleotides polymerized in one template binding event, and catalytic speed is in keeping with the rate of replication fork movement in E. coli, 1 kb/second at 37° C. (Chandler et al., 1975, J. Mol. Biol., vol. 94, pp 127–131).

Within Pol II, the $\alpha$ subunit (dnaE) contains the DNA polymerase activity (Blanar et al., 1984, Proc. Natl Acad. Sci. USA, vol. 81, pp 46224626), and the $\epsilon$ subunit (dnaQ, mutD) is the proofreading 3'–5' exonuclease (Scheuetmann and Echols, 1985, Proc. Natl Acad. Sci. USA, vol. 81, pp 7747–7751; DeFrancesco et al., 1984, J. Biol. Chem, vol. 259, pp 5567–5573). The $\alpha$ subunit forms a tight 1:1 complex with $\epsilon$ (Maki and Kornberg, 1985, J. Biol. Chem., vol. 260, pp 12987–12992). Whereas most DNA polymerases have 3'–5' exonuclease activity, only the holoenzyme relegates this activity to an accessory protein. The following three accessory proteins of the holoenzyme are known to be required for DNA replication as they are products of genes that are essential for cell viability: $\beta$ (dnaN) (Burgers et al., 1981, Proc. Natl Acad. Sci. USA, vol. 78, pp 5391–5395), $\tau$, and $\gamma$ (the latter two both encoded by the dnaXZ gene) (Kodaira et al., 1983, Mol. Gen. Genet., vol. 192, pp 80–86).

Important to the assessment of the individual functions of accessory proteins has been the availability of subassemblies of Pol Ill. Subassemblies include Pol III*, which is the holoenzyme lacking only $\beta$ (McHenry and Kornberg, 1977, J. Biol. Chem. vol. 252, pp 6478–6484); Pol III core, a heterotramer of $\alpha\epsilon\theta$ that contains the DNA polymerase $\alpha$ subunit and the proofreading 3'5' exonuclease $\epsilon$ subunit (McHenry and Crow, 1979, J. Biol. Chem., vol. 254, pp 1748–1753; Maki and Kornberg, 1985, J. Biol. Chem., vol. 260, pp 12987–12992; Scheuermann and Echols, 1985, Proc. Natl Acad Sci., vol. 81, pp 7747–7751); Pol III', a dimer of $\alpha\epsilon\theta\tau$ subunits (McHenry, 1982, J. Biol. Chem., vol. 257, pp 2657–2663); the $\gamma$ complex, $\gamma_2\delta\delta'\chi\Psi$, composed of 5 accessory proteins (Maki, and Kornberg, 1988, J. Biol. Chem., vol. 263, pp. 6555–6560); and a $\gamma\chi\Psi$ complex (O'Donnell, 1987, J. Biol. Chem. vol. 262, pp 16558–16565). Due to the low abundance of the holoenzyme in cells, these subassemblies have hitherto been available only in microgram quantities.

The core polymerase has weak catalytic efficiency and is only processive for approximately 11 nucleotides (Fay et al., 1981, J. Biol. Chem., vol. 256, pp 976–983). The catalytically efficient holoenzyme can be restored upon mixing core with both the $\beta$ and the $\gamma$ complex (Wickner, 1976, Proc. Natl Acad. Sci. USA, vol. 73, pp 3511–3515). Reconstitution of the holoenzyme proceeds in two stages. In the first stage, the $\gamma$ complex and the $\beta$ subunit hydrolyze ATP to form a tightly bound "preinitiation complex" clamped onto the primed DNA. In the second stage, the preinitiation complex binds the core and confers onto it highly processive synthesis. ATP is only required in the first stage.

The $\gamma$ complex both recognizes primed DNA and hydrolyzes ATP to clamp the $\beta$ subunit onto DNA. In fact, one $\gamma$ complex molecule can act catalytically to form many $\beta$ clamps on multiple DNA molecules (Stukenberg et al., 1991, J. Biol. Chem., vol. 266, pp 11328–11334). The $\gamma$ complex therefore has the characteristics of a chaperonin. Namely, it acts catalytically to couple ATP to assembly of a complex ("$\beta$.DNA"). Only the $\gamma$ and $\delta$ subunits are required to clamp $\beta$ onto primed DNA (O'Donnell, 1987, J. Biol. Chem., vol. 262, pp 16558–16665).

The holoenzyme Pol III is purified from E. coli as a multiprotein particle (O'Donnell, 1992, Bioessays, vol. 14, pp 105–111,). The probable orientations of the subunits within the holoenzyme can be deduce from the known interactions among subunits.

Both $\gamma$ and $\tau$ are produced from the same dnaXZ gene. The $\gamma$ subunit is produced by a frameshift event which occurs after approximately two thirds of the gene has been translated (Tsuchihashi and Kornberg, 1990, Proc. Natl Acad. Sci. USA, vol. 87, pp 2516–2520; Flower and McHerry, ibid. pp 3713–3717; Blinkowa and Walker, 1990, Nuc. Acids Res., vol. 18, pp 1725–1729). The frameshift is followed within two amino acids by a stop codon. The $\tau$ subunit is the full length product of the dnaXZ gene. Approximately equal amounts of $\tau$ and $\gamma$ are produced in E. coli (Kodaira et al., 1993, Mol. Gen. Genet., vol. 192, pp. 80–86).

One of the roles of the $\tau$ subunit is to serve as a scaffold to dimerize the polymerase subunits. One indication that $\tau$ dimerizes the polymerase is from the purification and characterization of the 4-protein (αεθτ) subassembly called Pol III'. Pol III' appears to be a dimer of all four subunits (McHenry, 1982, *J. Biol. Chem.*, vol. 257., pp 2657–2663). Since the αEθ Pol III core appears to contain only one of each subunit, the dimeric structure of Pol III' is believed to be due to the τ subunit. Study of pure α and τ subunits has shown the isolated α subunit, i.e., the polymerase is only a monomer, even at high concentration. However, the τ subunit, which is a dimer (Tsuchihashi and Kornberg, 1989, *J. Biol. Chem.*, vol. 264, pp 17790–17795), binds two molecules of α. Hence, τ appears to be the agent of polymerase dimerization. The τ subunit also increases the affinity of the core polymerase for the preinitiation complex (Maki and Kornberg, 1988, *J. Biol. Chem.*, vol. 263, pp. 6561–6569) and is a DNA-dependent ATPase, although the function of its ATPase activity is unknown (Lee and Walker, 1987, *Proc. Natl Acad. Sci. USA*, vol. 84, pp 2713–2717). The αεθ core polymerase appears to form a dimer when it is sufficiently concentrated. Since a 1:1 complex of αε shows no tendency to dimerize to (αε)$_2$, the θ subunit has also been proposed to aid polymerase dimerization (Maki et al., 1988, *J. Biol. Chem.*, vol. 263, pp 6570–6578). The β subunit also interacts with the core, specifically by direct interaction with α (O'Donnell 1987, *J. Biol. Chem.*, vol. 262, pp 16558–16565; LaDuca et al., 1986, *J. Biol. Chem.* vol. 261, pp 7550–7557). The γ subunit does appear to bind the polymerase subunit, implying it is the C-terminal portion of τ (lacking in γ) that binds α.

In determining the arrangement of the 5 subunits of the complex, isolation of a γχΨ complex suggests χ, Ψ, or both bind directly to γ. Neither χ nor Ψ have been found in association with τ. Possibly in γ, the omission of the C-terminal portion of τ yields a surface unique to γ which specifically binds χ and Ψ. Although it is not clear how the γ complex contacts the polymerase, the τ subunit can interact in vitro with either δ or δ' to form a complex that can lock β onto primed DNA (O'Donnell, 1987, *J. Biol. Chem.*, vol. 262, pp 16558–16565). This suggests that τ contacts the γ complex by interaction with δ and δ'.

DNA polymerases that duplicate chromosomes are remarkably processive multiprotein machines. These replicative polymerases remain in continuous association with the DNA over tens to hundreds of kilobases. The high processivity of Pol III holoenzyme lies in a ring-shaped protein that acts as a sliding clamp for the rest of the machinery. A ring-shaped sliding clamp is likely to be general for replicative polymerases, being formed by the PCNA protein of yeast and humans and the gene 45 protein of the T4 phage.

The subunit structure of the *E. coli* replicative polymerase is presented in Kornberg and Baker (Kornberg and Baker, 1991, *DNA Replication* W. H. Freeman, New York, pp 165–207). During purification, this multiprotein polymerase generally dissociates into three components: a DNA polymerase, a multisubunit accessory protein complex, and a single subunit accessory protein. The DNA polymerase components of *E. coli* are Pol III core, which is a heterotramer of α (polymerase), ε (3'5' exonuclease), and θ. Prokaryotic polymerases are not highly processive on their own; for this they require their respective accessory proteins. The accessory protein complex of *E. coli* is the five subunit γ complex, a DNA dependent ATPase that recognizes a primer-template junction. The single accessory subunit of *E. coli* is the β subunit, which has no inherent catalytic activity, but simulates the ATPases activity of the accessory protein complex.

The *E. coli* accessory proteins, γ complex plus β subunit, hydrolyze ATP to form a tight protein clamp (termed a "preititiation complex") on primed single-stranded (ss) DNA coated with ssDNA binding protein (Wickner, 1976, *Proc. Natl Acad. Sci. USA*, vol. 73, pp3511–3515; O'Donnell, 1987, *J. Biol. Chem.* vol. 262, pp 16558–16565; Maki and Kornberg, 1988, *J. Biol. Chem.*, vol. 263, pp 6561–6569). The core polymerase then associates with the preinitiation complex to form the highly processive holoenzyme. The preinitiation complex thus acts as a gliding clamp on primed DNA.

In the *E. coli* system, the γ complex can be separated from the preinitiation complex by gel filtration, leaving only a dimer of β on primed DNA. This dimer retains the capacity to confer highly processive synthesis onto the core polymerase (Stukenberg et al., 1991, *J. Biol. Chem.*, vol. 266, pp 11328–11334). Hence the γ complex is not required during processive elongation. The role of the γ complex is to recognize primed DNA and to couple ATP hydrolysis to clamp β onto DNA (Onrust et al., 1991, *J. Biol. Chem.*, vol. 266, pp 21681–21686). Only the γ and δ subunits are essential to clamp β onto DNA, although the other subunits of the γ complex modulate the activity of the γ and δ subunits (O'Donnell and Studwell, 1990, *J. Biol. Chem.*, vol. 265, pp 1179–1187).

Several β clamps can be transferred by one γ complex onto a single circular plasmid DNA molecule containing one nick (Stukenberg et al., op. cit.). These β clamps freely diffuse along the plasmid DNA and will slide off the end of this DNA if the circular plasmid is cut with a restriction enzyme. The sliding motion of β is bi-directional independent of ATP, and occurs only on duplex DNA (Stukenberg et al., op. cit.). It is known that β, once transformed by the γ complex into a strong DNA binding protein, readily slides off linear DNA. Hence it was hypothesized that the β dimer is shaped like a ring that encircles the duplex like a doughnut (Stukenberg et al., op cit.). This β ring can then slide off linear DNA like a washer off the end of a steel rod.

The β clamp confers processivity onto the core polymerase by binding directly to the polymerase α subunit, thereby tethering the polymerase to DNA for processive syntheses. As the polymerase extends the 3' terminus, it simply pulls the β sliding clamp along.

X-ray analysis of β shows that it indeed has the shape of a ring (Kong et al., 1992, *Cell* vol. 67, pp 425–437). The central cavity is of sufficient diameter to accommodate duplex DNA and is lined with 12 α helices that are supported by a single continuous layer of β sheet structure all around the outside. Although the β ring is uninterrupted and looks like a single molecule, it is actually a head-to-tail dimer. The width of the β clamp is approximately that of one turn of the DNA helix, and the head-to-tail arrangement creates physically distinct front and back faces. The "A" face is rather flat and is more negatively charged than the "B" face, which is characterized by several loops. The γ complex likely opens and closes the β ring around DNA and orients the correct face toward the primer terminus for interaction with the polymerase. Each β monomer is composed of three domains that have the same three-dimensional structure, giving the β dimer a six-fold repeat appearance. This high degree of symmetry in the β ring could help promote smooth gliding along the symmetrical DNA duplex.

The β clamp is negatively charged overall, but the α helices lining the central cavity are positively charged, perhaps to stabilize the β clamp on DNA. Ionic interaction between β and DNA must be mediated by water because the inside diameter of the β ring is too large for direct contact between the basic side chains and the DNA at the center. The lack of direct contact between β and DNA may facilitate the sliding motion.

It is not clear why the clamp is separate from the polymerase, but it seems likely that there are advantages in having a separate clamp. For example, the lagging strand is synthesized as a series of short fragments, and in *E. coli* the polymerase must complete a fragment then dissociate from it and reassociate with a new primer made by primase all within a second. Biochemical studies show that the polymerase core rapidly dissociates from its β clamp, but only after DNA synthesis is complete, and then it reassociates with another β clamp on a new primed template (O'Donnell, 1981, *J. Biol. Chem.* vol. 262, pp 16588–16565; Studwell et al., 1990, *UCLA Symp. Mol. Cell Biol. New Ser.*, vol. 127, pp 153–164). Hence, rapid disassembly/reassembly of the polymerase with separate β clamps may provide a mechanism by which a highly processive polymerase can rapidly recycle on and off DNA during syntheses of the numerous lagging strand fragments.

SUMMARY OF THE INVENTION

The present invention relates to a number of processes for reconstituting polymerase III* and other subassemblies of *E. coli* DNA polymerase III holoenzyme.

One embodiment of the present invention relates to a process for reconstituting the polymerase III* subassembly of *E. coli* DNA polymerase III holoenzyme from peptide subunits $\gamma$, $\tau$, $\alpha$, $\epsilon$, $\theta$, $\delta$, $\delta'$, $\chi$, and $\Psi$ by: combining the subunits in any order under conditions effective to form the polymerase III* subassembly, provided that $\gamma$ is joined with $\tau$ in a single complex prior to incorporating $\delta$ in that complex.

Another embodiment of the present invention relates to a process for reconstituting the polymerase III* subassembly of *E. coli* DNA polymerase III holoenzyme by:
(a) providing a $\gamma\tau\chi\Psi$ complex;
(b) providing an $\alpha\epsilon\theta$ core complex; and
(c) combining the $\gamma\tau\chi\Psi$ complex, the $\alpha\epsilon\theta$ core complex, $\delta$, and $\delta'$ under conditions effective to form the polymerase III* subassembly.

Another embodiment of the present invention relates to a process for reconstituting the polymerase III* subassembly of *E. coli* DNA polymerase III holoenzyme from the substantially pure peptide subunits $\gamma$, $\tau$, $\alpha$, $\epsilon$, $\theta$, $\delta$, $\delta'$, $\chi$, and $\Psi$ by: combining $\gamma$, $\Psi$, and $\delta'$ or $\tau$, $\Psi$, and $\delta'$ under conditions effective to form, respectively, substantially pure $\gamma\Psi\delta'$ complex or substantially pure $\tau\Psi\delta'$ complex; combining the $\gamma\Psi\delta'$ complex with $\tau$ or the $\tau\Psi\delta'$ complex with $\gamma$ under conditions effective to form $\gamma\tau\Psi\delta'$ complex; and combining the $\gamma\tau\Psi\delta'$ complex with $\alpha$, $\epsilon$, $\theta$, $\delta$, and $\chi$ in any order under conditions effective to form the polymerase III* subassembly.

Another embodiment of the present invention relates to a process for reconstituting the polymerase III* subassembly of *E. coli* DNA polymerase III holoenzyme by:
(a) providing a $\gamma\chi\Psi\delta'$ complex;
(b) providing an $\alpha\epsilon\theta$ core complex;
(c) combining the $\gamma\chi\Psi\delta'$ complex with $\tau$ under conditions effective to form a $\gamma\tau\chi\Psi\delta'$ complex;
(d) combining the $\gamma\tau\chi\Psi\delta'$ complex with $\delta$ under conditions effective to form a $\gamma\tau\chi\Psi\delta\delta'$ complex; and
(e) combining the $\gamma\tau\chi\Psi\delta\delta'$ complex and the $\alpha\epsilon\theta$ core complex under conditions effective to form the polymerase III* subassembly.

Another embodiment of the present invention relates to a process for reconstituting the polymerase III* subassembly of *E. coli* DNA polymerase III holoenzyme by:
(a) providing $\tau\chi\Psi\delta'$ complex;
(b) providing an $\alpha\epsilon\theta$ core complex;
(c) combining the $\tau\chi\Psi\delta'$ complex with $\gamma$ under conditions effective to form a $\gamma\tau\chi\Psi\delta'$ complex;
(d) combining the $\gamma\tau\chi\Psi\delta'$ complex with $\delta$ under conditions effective to form a $\gamma\tau\chi\Psi\delta\delta'$ complex; and
(e) combining the $\gamma\tau\chi\Psi\delta\delta'$ complex with the $\alpha\epsilon\theta$ core complex under conditions effective to form the polymerase III* subassembly.

Another embodiment of the present invention relates to a process for reconstituting the polymerase III* subassembly of *E. coli* DNA polymerase III holoenzyme by:
(a) providing a $\gamma\Psi\delta'$ complex;
(b) combining the $\gamma\Psi\delta'$ complex with $\tau$ under conditions effective to form $\gamma\tau\Psi\delta'$ complex; and
(c) combining the $\gamma\tau\Psi\delta'$ complex with $\alpha$, $\epsilon$, $\theta$, $\delta$, and $\chi$ in any order under conditions effective to form the polymerase III* subassembly.

Another embodiment of the present invention relates to a process for reconstituting the polymerase III* subassembly of *E. coli* DNA polymerase III holoenzyme by:
(a) providing a $\tau\Psi\delta'$ complex;
(b) combining the $\tau\Psi\delta'$ complex with y under conditions effective to form $\gamma\tau\Psi\delta'$ complex; and
(c) combining the $\gamma\tau\Psi\delta'$ complex with $\alpha$, $\epsilon$, $\theta$, $\delta$ and $\chi$ in any order under conditions effective to form the polymerase III* subassembly.

The present invention also relates to a process for reconstituting the γ-less Pol III* subassembly from subunits $\tau$, $\alpha$, $\epsilon$, $\theta$, $\delta$, $\delta'$, $\chi$ and $\Psi$ by: combining $\tau$, $\alpha$, $\epsilon$, $\theta$, $\delta$, $\delta'$, $\chi$ and $\Psi$ in any order under conditions effective to form the γ-less Pol III* subassembly.

Another assect of the present invention relates to a process for reconstituting an $\alpha\tau\chi\Psi\delta\delta'$ subassembly from subunits $\tau$, $\alpha$, $\delta$, $\delta'$, $\chi$, and $\Psi$ by: combining $\tau$, $\alpha$, $\delta$, $\delta'$, $\chi$, and $\Psi$ in any order under conditions effective to form the $\alpha\tau\chi\Psi\delta\delta'$ subassembly.

Still another aspect of the present invention relates to a process for reconstituting an $\alpha\tau\delta\delta'$ subassembly from $\tau$, $\alpha$, $\delta$, and $\delta'$ by: combining $\tau$, $\alpha$, $\delta$, and $\delta'$ in any order under conditions effective to form the $\alpha\tau\delta\delta'$ subassembly.

The present invention also relates to a process for reconstituting an $\alpha\epsilon\theta\tau\delta\delta'$ subassembly from subunits $\tau$, $\alpha$, $\epsilon$, $\theta$, $\delta$, and $\delta'$ by: combining $\tau$, $\alpha$, $\epsilon$, $\theta$, $\delta$, and $\delta'$ in any order under conditions effective to form the $\alpha\epsilon\theta\tau\delta\delta'$ subassembly.

DETAILED DESCRIPTION OF THE INVENTION

Figure 1:
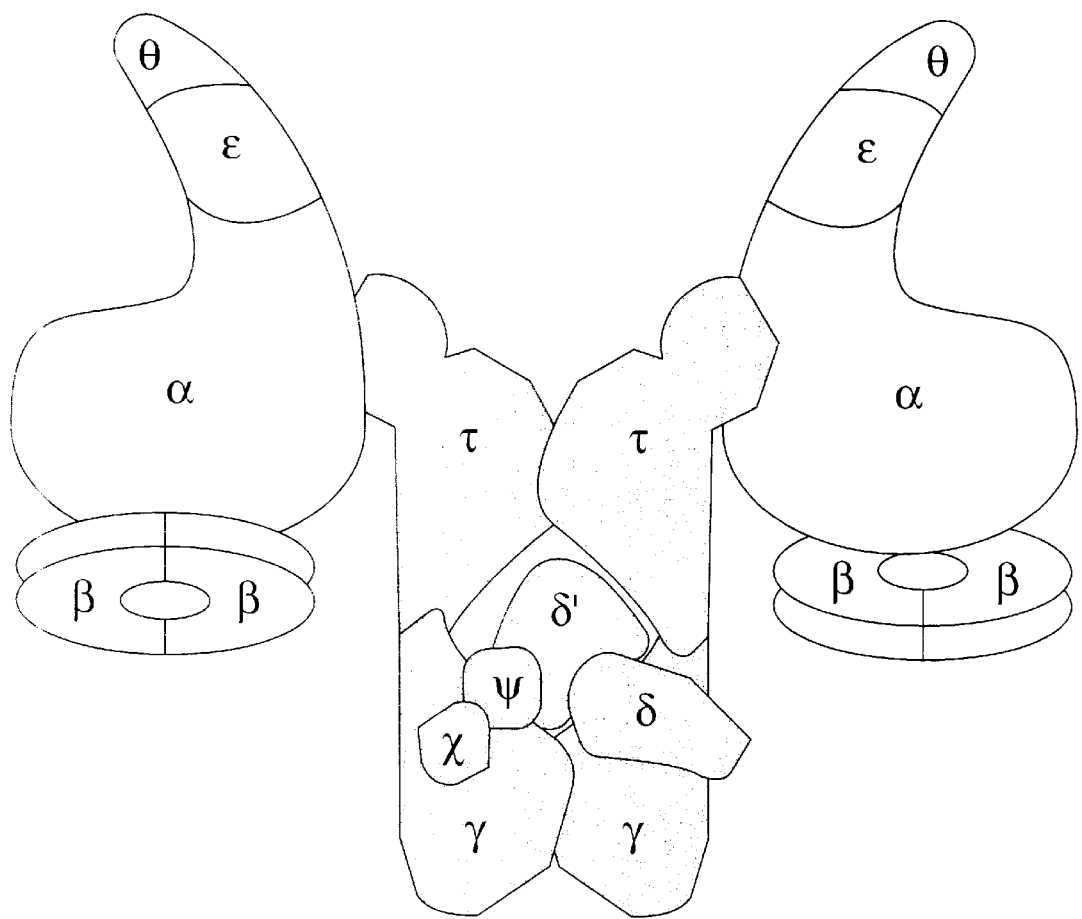
FIG. 1 is a schematic representation of the protein subunits in the Pol III holoenzyme.

Pol III holoenzyme has traditionally been difficult to obtain in large quantity because of its low cellular concentration, only 10–20 molecules per cell (O'Donnell, 1992, *Bioessays*, vol. 14, pp 105–111). However, all ten subunits comprising Pol III are now available in abundance by molecular cloning of their genes and high level expression techniques, as disclosed in the following publications, the disclosures of which are incorporated herein by reference: Onrnst, R., O'Donnell, M., 1993, *DNA polymerase III accessory proteins. II Characterization of δ and δ'. J. Biol. Chem.* vol. 268, pp. 11766–11772; Dong, A., Onrist, R, Skangalis, M., and O'Donnell, M., 1993, *DNA polymerase III accessory proteins. I. holA and holB encoding δ and δ'. J. Biol. Chem.*, vol. 268, pp 11758–11765; Xiao, H., Crombie, R,. Dong, Z., Onrust, R, and O'Donnell, M., 1993, *DNA polymerase III accessory proteins. III holC and holD encoding χ and Ψ. J. Biol. Chem.* vol. 268, pp 11773–11778; Xiao, H., Dong, Z., and O'Donnell, M., 1993, *DNA polymerase III accessory proteins. IV. Characterization of χ and Ψ. J. Biol. Chem.*, vol. 268, pp 11773–11778; Studwell-Vaughan, P. S. and O'Donnell, M., 1993, *DNA polymerase III accessory proteins. V. θ encoded by holE. J. Biol. Chem.*, vol. 268, pp 11785–11791; Carter, J. R., Franden, M. A., Aebersold, R., and McHenry, C. S., 1993, *Molecular cloning, sequencing, and overexpression of the structural gene encoding the δ subunit of E. coli DNA polymerase III holoenzyme. J. Bacteriol.*, vol. 174, pp7013–7025; Carter, J. R., Franden, M. A., Aebersold, R., and McHenry, C. S., 1993, *Identification, isolation, and characterization of the structural gene encoding the δ' subunit of E. coli DNA polymerase III holoenzyme. J. Bacteriol*, vol. 175, pp 3812–3822; Carter, J. R., Franden, M. A., Aebersold, R., Kim, D. R, and McHenry, C. S., 1993, *Isolation sequencing and overexpression of the gene encoding the θ subunit of DNA polymerase III holoenzyme. Nuc. Acids Res.*, vol. 21, pp 3281–3286; Carter, J. R., Franden, M. A., Aebersold, R., and McHenry, C. S., 1993, *Identification, isolation, and overexpression of the gene encoding the Ψ subunit of DNA polymerase III holoenzyme. J. Bacteriol.*, vol. 175, pp 5604–5610; and Carter, J. R, Franden, M. A., Lippincott, J. A., and McHenry, C. S., 1993, *Identification, molecular cloning and characterization of the gene encoding the χ subunit of DNA polymerase III holoenzyme of E. coli. Mol. Gen. Genet.* vol. 241, pp 399–408. The gene sequences for these subunits are also disclosed in the following references; the disclosures of which are incorporated herein by reference: O'Donnell, International Application No. WO93/15115, filed Jan. 24, 1993; Tomasiewicz and McHenry, 1987, *J. Bacteriol. vol.* 169, pp 5735–5744; Ohmori et al., 1984, *Gene.* vol. 28, pp 159–170; Flower and McHenry, 1986, *Nuc. Acids Res., vol.* 14, pp 8091–8101; Ym et i., ibid. pp 6541–6549; and Maki et al., 1983, *Proc. Natl Acad. Sci. USA*, vol. 80, pp 7137–7141. Using the nucleotide sequences, the protein subunits can be obtained by conventional recombinant DNA techniques. The availability of the substantially pure subunits makes possible the reconstitution of the polymerase III* subassembly, Pol III*, of Pol III holoenzyme in accordance with the methods of the present invention. The β subunit can be added to the, Pol III* subassembly to complete the structure of the holoenzyme, as described in Lasken and Kornberg, 1987, *J. Biol. Chem.*, vol. 262, pp 1720–1724, the disclosures of which are incorporated herein by reference.

In accordance with the present invention, the 9-subunit Pol III* assembly is constituted from individual pure proteins; it is the same size and is as active as Pol III* purified naturally from *E. coli*. The particle contains 14 polypeptides in an arrangement consisting of two core polymerases and a γ complex clamp loader all connected to each other through τ, as illustrated in FIG. 1. Two core polymerases are bound to a τ dimer, most likely one on each protomer of τ. Assuming the τ is in an isologous arrangement, each polymerase-τ protomer unit is related to the other by a 2-fold axis of rotation and therefore τ is not oriented asymmetric relative to the two polymerases. The τ dimer forms a heterotramer with γ, and assuming the tetramer is an isologous arrangement, the Pol III'-γ interaction is also perfectly symmetric having a 2-fold rotational axis relating each unit [core-τ protomer-γ protomer] to the other unit. However, the single copy each of δ, δ', χ and Ψ imposes a structural asymmetry onto the structure of Pol III* such that there can be no overall 2-fold rotational axis. Presumably the structure asymmetry created by these single copy subunits imposes a functional asymmetry onto the two polymerases for the different actions needed on the leading and lagging strands. Whether these subunits are all on δ, or whether they are on τ is discussed below. The β subunit associates with the α subunit of the core polymerase (Studwell-Vaughan and O'Donnell, 1991,*J. Biol. Chem.* vol. 266, pp 19833–19841), and with the δ subunit of the γ complex; therefore a total of three β dimers may associate with Pol III*. Two β dimers are present in the holoenzyme; in FIG. 12 they are shown on the two corepolymerases.

In the Pol III holoenzyme, all of the subunits of the holoenzyme except τ and γ are monomers in isolation. The oligomeric structure of τ is needed to bring two copies of the core polymerase into the Pol III* structure. Further, the holoenzyme architecture contains only one each of the δ, δ', χ and Ψ subunits. Since either τ or γ can bind these single copy subunits, it seems plausible that the Pol III holoenzyme would obtain at least two copies of each of them, a set on γ and a set on τ. However, the holoenzyme architecture precludes this by preventing the $\iota_2\tau_2$ complex from binding more than one δ' monomer—perhaps by allotting only enough space inside the junction of the heterotramer to fit one monomer of δ' (as suggested in FIG. 1). The ability to place only one δ' monomer in Pol III* is consistent with the observed stoichiometry of one δ' in Pol III* and is also in keeping with the single copy of δ in Pol III*, as it has been shown that δ-δ' form a 1:1 complex (Onrust and O'Donnell, 1993, *J. Biol. Chem.*, vol. 268, pp 11766–11772).

The χ and Ψ subunits can be bound to both γ and τ at the same time without inhibiting the assembly of the τ-γ interaction. Thus it seems possible that Pol III* could in principle have two copies of χ and Ψ, but the stoichiometry studies (discussed below) suggest only one of each is present in Pol III*. It has been found that the χΨ complex dissociates easily from γ (and τ), but that addition of δδ' greatly stabilizes the χΨ-to-γ interaction. Hence, it may be presumed that whichever dimer, γ or τ, that the δδ' complex is associated with in Pol III* will also be the dimer with which the χΨ complex stably associates. In other words, the enhanced stability incurred by the presence of all these subunits on γ provides the explanation for the single copy of χ and Ψ in Pol III*; the χΨ complex that is stabilized through interaction with δδ' (e.g. on γ) will remain in Pol III*, while the χΨ complex lacking the stabilization provided by δδ' (e.g. on τ) will be easily shed from the structure.

The subunit arrangement of Pol III* shown in FIG. 1 differs from that proposed by Malid et al., 1988, *J. Biol. Chem.*, vol. 263, pp 6570–6578, in which one core polymerase was on τ and the other core was on γ. This asymmetric arrangement of subunits was proposed to endow each polymerase with different properties, one suited for continuous synthesis of the leading stand and the other for discontinuous synthesis of the lagging strand. The arrangement in FIG. 1 differs from the earlier study in that a τ dimer bridges both polymerases and γ binds the polymerase indirectly, through the τ dimer. In support of this, no interaction of core to γ or to any other subunit of the γ complex, or to the entire γ complex, has been detected Both models propose that the δ, δ', χ and Ψ subunits are associated with the γ dimer; FIG. 1 shows that the asymmetric structure of Pol III* is based in the single copy nature of these subunits. The earlier study of Pol III* structure, however, proposed two copies of each subunit in Pol III*, but this stoichiometry does not match the known 2:1:1:1:1 stoichiometry of the γ complex (Maki et al., 1988, *J. Biol. Chem.*, vol. 265, pp 6555–6560), and is inconsistent with the stoichiometry of subunits in the holoenzyme performed in the earlier study, which was more consistent with one subunit each of δ, δ', χ and Ψ, and two subunits each of α, ε, θ, τ and γ. This discrepancy might be explained by free γ complex being present in the naturally purified Pol III* preparation, which would have increased the apparent stoichiometry of the δ, δ', χ and Ψ subunits.

Since the δ, δ', χ and Ψ single copy subunits can be added after mixing τ with γ, there is some question as to their exact position, whether they are on γ or τ, or split between them, or shared. Since δ' can be placed on either γ or τ followed by assembly of Pol III*, the δ' subunit may be on either τ or γ, but not on both at the same time. Since δ must be added last, it may assemble with the τ or γ subunit, presumably the one that has δ'. It has been found that the presence of core on τ slows down the association kinetics of δ' and χΨ to τ considerably. Hence, in the presence of core, there appears to be a kinetic bias for association of the single copy subunits with γ father than τ. Consistent with this, Pol III' purified from *E. coli* does not contain the χΨ subunits, nor has a τ complex been purified from *E. coli*, consistent with γ as the preferred target of association of these single copy subunits.

Despite these arguments of δ, δ', χ and Ψ being associated with γ instead of τ in Pol III*, it is still conceivable that γ and τ share these subunits either in time (by dissociation and reassociation of δ' between γ and τ), or physically in which the δ, δ', χ and Ψ subunits bridge the τ/γ boundary, with some present on γ and some on τ. For example, δ' shows weak, but detectable, clamp loading activity with τ, but not with δ, thereby presenting the possibility of two clamp loaders in Pol III* consisting of τδ' and γδ (Onrust and O'Donnell, 1993, *J. Biol. Chem.*, vol. 268, pp 11766–11772; O'Donnell and Studwell, 1990, *J. Biol. Chem.*, vol. 265, pp. 1179–1187).

Although τ complex has not been purified from wild type *E. coli*, a τ complex and a γ-less form of Pol III* can be reconstituted from individual subunits, and these assemblies are active in replication assays, as discussed in Blinkova et al., 1993, *J. Bacteriol.*, vol. 175, pp. 6018–6027, the disclosures of which are incorporated by herein by reference. Whether such complexes function in vivo is unknown, but it has been reported that *E. coli* cells are viable in which the signal for the -1 translational frameshift that produces γ is removed (Blinkova et al., ibid. These cells contain only the τ subunit and the γ-less Pol III*, implying that γ-less Pol III* can function at a replication fork.

The core polymerase appears to slow down the association of δ' and χΨ complex with τ, but not with γ, and thus the single copy subunits may be expected to locate themselves on γ as discussed above. However, by staging the assembly of Pol III* in vitro, it should be possible to selectively place the δδ'χΨ subunits on τ by preincubating them with τ in the absence of γ. For example, Pol III* can be constituted starting from τχΨδ' complex, followed by adding γ, then δ and core. Provided the subunits do not exchange from τ-to-γ during the assembly time (a real possibility), the resulting Pol III* should at least have δ'χΨ on τ rather than on γ.

In addition to Pol III*, other subassemblies of the polymerase III holoenzyme may be useful, when employed with the β clamp, for achieving good DNA sequencing ladders. For example, the "γ-less Pol III*" subassembly, whose composition is postulated to be $(\alpha\epsilon\theta)_4\tau_4\chi\Psi\delta\delta'$, contains the polymerase core complex αεθ and the clamp-loading complex χΨδδ'; both attached to τ. γ-less Pol III*, which exhibited specific activity substantially higher than either purified natural Pol III* or reconstituted Pol III*, can be formed by combining the component protein subunits in any order. In one procedure, the τχΨδδ' containing the clamp loader is formed first, followed by combination with the α, ε, and θ subunits that comprise the polymerase core complex.

The just described τχΨδδ' complex can also be combined with the α polymerase subunit to form an ατχΨδδ' subassembly, a lower weight analog of γ-less Pol III*.

It is desirable to form other relatively small subassemblies of the Pol III holoenzyme, which would allow for simplified preparation and isolation procedures. For example, a τδ' clamp loading complex or its component subunits can be combined with core complex αεθ or its component subunits to form an as αεθτδ' subassembly. An even smaller subassembly can be obtained by combining the τδ' complex or its component subunits with the polymerase subunit α.

Pol III* Reconstitution Process A

One embodiment of the present invention relates to a process for reconstituting the polymerase III* subassembly of *E. coli* DNA polymerase III holoenzyme from peptide subunits γ, τ, α, ε, θ, δ, δ, ', χ, and Ψ by: combining the subunits in any order under conditions effective to form the polymerase III* subassembly, provided that γ is joined with τ in a single complex prior to incorporating δ in that complex.

The process further comprises combining the polymerase III* subassembly with β to form the polymerase III holoenzyme.

Pol III* Reconstitution Process B

Another embodiment of the present invention relates to a process for reconstituting the polymerase III* subassembly of *E. coli* DNA polymerase III holoenzyme by:

(a) providing a γτχΨ complex;

(b) providing an αεθ core complex; and (c) combining the γτχΨ complex, the αεθ core complex, δ, and δ' under conditions effective to form the polymerase III* subassembly.

The process further comprises combining the polymerase III* subassembly with β to form the polymerase III holoenzyme.

In accordance with the invention, the provided γτχΨ complex can be formed from the component subunits in various ways, for example:

(1) combining the component subunits γ, τ, χ, and Ψ;
(2) combining γ and Ψ to form a γΨ complex, and then combining the χΨ complex with τ and χ;
(3) combining τ with Ψ to form a τΨ complex, and then combining the τΨ complex with γ and τ;
(4) combining χ, Ψ, and γ to form a γχΨ complex, and then combining the τχΨ complex with τ;
(5) combining χ, Ψ, and τ to form a τχΨ complex, and then combining the τχΨ complex with γ;
(6) combining χ and Ψ to form a χΨ complex, and then combining the χΨ complex with γ and τ;
(7) combining the χΨ complex with γ to form a γχΨ complex, and then combining the γχΨ complex with τ;
(8) combining the χΨ complex with τ to form a τχΨ complex, and then combining the τχΨ complex with γ; or
(9) combining the γχΨ complex with the τχΨ complex.

In one embodiment of the process of the invention, combining χ, Ψ, and τ and combining χ, Ψ, and γ comprises:

forming an aqueous composition (1) comprising subunits χ and Ψ and incubating composition (1) under conditions effective to form a composition (1') comprising χΨ complex;

forming an aqueous composition (2) comprising a first portion of composition (1') and subunit τ and incubating composition (2) under conditions effective to form a composition (2') comprising τχΨ complex; and forming an aqueous composition (3) comprising a second portion of composition (1') and subunit γ and incubating composition (3) under conditions effective to form a composition (3') comprising γχΨ complex, wherein the combining γχΨ complex and τχΨ complex comprises:

forming an aqueous composition (4) comprising compositions (2') and (3') and incubating composition (4) under conditions effective to form a composition (4') comprising γτχΨ complex, wherein providing an αεθ core complex comprises:

forming an aqueous composition (6) comprising subunits α, ε, and θ and incubating composition (6) under conditions effective to form a composition (6') comprising core complex αεθ, wherein combining the γτχΨ complex, the αεθ core complex, δ, and δ' comprises:

forming an aqueous composition (5) comprising composition (4') and subunit δ and δ' and incubating composition (5) under conditions effective to form a composition (5');

forming an aqueous composition (7) comprising compositions (5') and (6') and incubating composition (7) under conditions effective to form a composition (7') comprising the polymerase III* subassembly; and separating polymerase III* subassembly from composition (7').

In another embodiment of the process of the invention, combining χ, Ψ, and τ comprises:

forming an aqueous composition (1) comprising subunits χ and Ψ and incubating the composition (1) under conditions effective to form a composition (1') comprising χΨ complex and forming an aqueous composition (2) comprising a first portion of composition (1') and τ and incubating composition (2) under conditions effective to form a composition (2') comprising τχΨ complex, wherein combining the τχΨ complex with γ comprises:

forming an aqueous composition (8) comprising τχΨ complex and subunit γ and incubating composition (8) under conditions effective to form a composition (8') comprising γτχΨ complex, wherein providing an αεθ complex comprises:

forming an aqueous composition (6) comprising subunits α, ε, and θ, incubating composition (6) under conditions effective to form a composition (6') comprising core complex αεθ, wherein combining the γτχΨ complex, the core complex αεθ, δ, and δ' comprises:

forming an aqueous composition (5) comprising composition (8') and subunits δ and δ' and incubating composition (5) under conditions effective to form a composition (5') comprising γτχΨδδ' complex;

forming an aqueous composition (7) comprising compositions (5') and (6') and incubating composition (7) under conditions effective to form a composition (7') comprising polymerase III* subassembly; and separating the polymerase III* subassembly from the composition (7').

In still another embodiment of the process of the invention, combining χ, Ψ, and γ comprises:

forming an aqueous composition (1) comprising subunits χ and Ψ and incubating composition (1) under conditions effective to form a composition (1') comprising χΨ complex and forming an aqueous composition (3) comprising a first portion of composition (1') and γ and incubating composition (3) under conditions effective to form a composition (3') comprising γχΨ complex, wherein combining the γχΨ complex with τ comprises:

forming an aqueous composition (9) comprising γχΨ complex and subunit τ and incubating composition (9) under conditions effective to form a composition (9') comprising γτχΨ complex, wherein providing an αεθ complex comprises:

forming an aqueous composition (6) comprising subunits α, ε, and θ, incubating composition (6) under conditions effective to form a composition (6') comprising core complex αεθ, wherein combining γτχΨ complex, the core complex αεθ, δ, and δ' comprises:

forming an aqueous composition (5) comprising composition (9') and subunits δ and δ' and incubating composition (5) under conditions effective to form a composition (5') comprising γτχΨδδ' complex;

forming an aqueous composition (7) comprising composition (5') and composition (6') and incubating composition (7) under conditions effective to form a composition (7') comprising polymerase III* subassembly; and separating the polymerase III* subassembly from said composition (7').

Pol III* Reconstitution Process C

Another embodiment of the present invention relates to a process for reconstituting the polymerase III* subassembly of E. coli DNA polymerase III holoenzyme from the substantially pure peptide subunits $\gamma$, $\tau$, $\alpha$, $\epsilon$, $\theta$, $\delta$, $\delta'$, $\chi$, and $\Psi$ comprises: combining $\gamma$, $\Psi$, and $\delta'$ or $\tau$, $\Psi$, and $\delta'$ under conditions effective to form, respectively, substantially pure $\gamma\Psi\delta'$ complex or substantially pure $\tau\Psi\delta'$ complex; combining the $\gamma\Psi\delta'$ complex with $\tau$ or the $\tau\Psi\delta'$ complex with $\gamma$ under conditions effective to form $\gamma\tau\Psi\delta'$ complex; and combining the $\gamma\tau\Psi\delta'$ complex with $\alpha$, $\epsilon$, $\theta$, $\delta$, and $\chi$ in any order under conditions effective to form the polymerase III* subassembly.

The process further comprises combining the polymerase III* subassembly with $\beta$ to form the polymerase III holoenzyme.

Pol III* Reconstitution Process D

Another embodiment of the present invention relates to a process for reconstituting the polymerase III* subassembly of E. coli DNA polymerase III holoenzyme by:

(a) providing a $\gamma\chi\Psi\delta'$ complex;

(b) providing an $\alpha\epsilon\theta$ core complex;

(c) combining the $\gamma\chi\Psi\delta'$ complex with $\tau$ under conditions effective to form a $\gamma\tau\chi\Psi\delta'$ complex;

(d) combining the $\gamma\tau\chi\Psi\delta'$ complex with $\delta$ under conditions effective to form a $\gamma\tau\chi\Psi\delta\delta'$ complex; and (e) combining the $\gamma\tau\chi\Psi\delta\delta'$ complex and the $\alpha\epsilon\theta$ core complex under conditions effective to form the polymerase III* subassembly.

The subunits $\chi$ and $\Psi$ can be combined to form a $\chi\Psi$ complex, which can be combined with $\gamma$ and $\delta'$ to provide the $\gamma\chi\Psi\delta'$ complex. The $\gamma\chi\Psi\delta'$ complex can be combined with $\tau$ to form a $\gamma\tau\chi\Psi\delta'$ complex, which can be combined with $\delta$ to form a $\gamma\tau\chi\Psi\delta\delta'$ complex.

The process further comprises combining the polymerase III* subassembly with $\beta$ to form the polymerase III holoenzyme.

In another embodiment of the process of the invention, providing a $\gamma\chi\Psi\delta'$ complex comprises:

forming an aqueous composition (1) comprising subunits $\chi$ and $\Psi$ and incubating composition (1) under conditions effective to form a composition (1') comprising $\chi\Psi$ complex;

forming an aqueous composition (10) comprising composition (1') and subunits $\delta'$ and $\gamma$, and incubating composition (10) under conditions effective to form a composition (10') comprising $\gamma\chi\Psi\delta'$ complex; and separating $\gamma\chi\Psi\delta'$ complex from composition (10'), wherein combining $\gamma\chi\Psi\delta'$ complex with $\tau$ comprises:

forming an aqueous composition (11) comprising composition (10') and subunit $\tau$ and incubating composition (11) under conditions effective to form a composition (11') comprising $\gamma\tau\chi\Psi\delta'$ complex, wherein combining $\gamma\tau\chi\Psi\delta'$ complex with $\tau$ comprises:

forming an aqueous composition (12) comprising composition (11') and subunit $\delta$ and incubating composition (12) under conditions effective to form a composition (5') comprising $\gamma\tau\chi\Psi\delta\delta'$ complex, wherein providing an $\alpha\epsilon\theta$ complex comprises:

forming an aqueous composition (6) comprising subunits $\alpha$, $\epsilon$, and $\theta$ and incubating composition (6) under conditions effective to form a composition (6') comprising core complex $\alpha\epsilon\theta$, wherein combining $\gamma\tau\chi\Psi\delta\delta'$ complex comprises:

forming an aqueous composition (7) comprising compositions (5') and (6') and incubating composition (7) under conditions effective to form a composition (7') comprising the polymerase III* subassembly; and separating the polymerase III* subassembly from composition (7').

The process further comprises combining the polymerase III* subassembly with $\beta$ to form the polymerase III holoenzyme.

Pol III* Reconstitution Process E

Another embodiment of the present invention relates to a process for reconstituting the polymerase III* subassembly of E. coli DNA polymerase III-holoenzyme by:

(a) providing a $\tau\chi\Psi\delta'$ complex;

(b) providing an $\alpha\epsilon\theta$ core complex;

(c) combining the $\tau\chi\Psi\delta'$ complex with $\gamma$ under conditions effective to form a $\gamma\tau\chi\Psi\delta'$ complex;

(d) combining the $\gamma\tau\chi\Psi\delta'$ complex with $\delta$ under conditions effective to form a $\gamma\tau\chi\Psi\delta\delta'$ complex; and (e) combining the $\gamma\tau\chi\Psi\delta\delta'$ complex with the $\alpha\epsilon\theta$ core complex under conditions effective to form the polymerase III* subassembly.

The process further comprises combining the polymerase III* subassembly with $\beta$ to form the polymerase III holoenzyme.

The core complex $\alpha\epsilon\theta$ can be formed by combining the component subunits under reaction conditions effective for its formation.

The $\gamma\tau\chi\Psi\delta\delta'$ complex can be formed by sequences such as the following:

(1) combining $\gamma\tau$ complex with $\chi$, $\Psi$, $\delta$, and $\delta'$;

(2) combining $\gamma\tau\chi\Psi$ complex with $\delta$ and $\delta'$;

(3) combining $\gamma\tau\Psi\delta'$ complex with $\chi$ and $\delta$; or (4) combining $\gamma\tau\Psi\delta'$ complex with $\tau$ to form $\gamma\tau\chi\Psi\delta'$ complex, which is combined with $\delta$.

By combining the core complex $\alpha\epsilon\theta$ and the $\gamma\tau\chi\Psi\delta\delta'$ complex under effective conditions, the polymerase III* subassembly can be formed.

The $\gamma\chi\Psi\delta\delta'$ complex can be formed, for example, by combining $\chi$ and $\Psi$ to form $\chi\Psi$ complex, which is combined with $\gamma$ and $\delta'$. Similarly, the $\tau\chi\Psi\delta'$ complex can be formed by combining the $\chi\Psi$ complex with $\tau$ and $\delta'$.

In a further embodiment of the process of the invention, providing a $\tau\chi\Psi\delta'$ complex comprises:

forming an aqueous composition (1) comprising subunits $\chi$ and $\Psi$ and incubating composition (1) under conditions effective to form a composition (1') comprising $\chi\Psi$ complex;

forming an aqueous composition (13) comprising composition (1') and subunits $\delta'$ and dimeric $\tau$, and incubating composition (13) under conditions effective to form a composition (13') comprising $\tau\chi\Psi\delta'$ complex; and separating $\tau\chi\Psi\delta\delta'$ complex from composition (13'), wherein combining $\tau\chi\Psi\delta'$ complex with $\gamma$ comprises:

forming an aqueous composition (14) comprising composition (13') and subunit $\gamma$ and incubating composition (14) under conditions effective to form a composition (14') comprising $\gamma\tau\chi\Psi\delta'$ complex, wherein combining $\gamma\tau\chi\Psi\delta'$ complex with $\delta$ comprises:

forming an aqueous composition (15) comprising composition (14') and subunit $\delta$ and incubating composition (15) under conditions effective to form a composition (5') comprising $\gamma\tau\chi\Psi\delta\delta'$ complex, wherein providing an $\alpha\epsilon\theta$ core complex comprises:

forming an aqueous composition (6) comprising subunits $\alpha$, $\epsilon$, and $\theta$ and incubating composition (6) under conditions effective to form a composition (6') comprising core complex $\alpha\epsilon\theta$, wherein combining $\gamma\tau\chi\Psi\delta\delta'$ complex comprises:

forming an aqueous composition (7) comprising compositions (5') and (6') and incubating composition (7) under conditions effective to form a composition (7') comprising the polymerase III* subassembly; and separating the polymerase III* subassembly from composition (7').

Pol III* Reconstitution Process F

Another embodiment of the present invention relates to a process for reconstituting the polymerase III* subassembly of E. coli DNA polymerase III holoenzyme by:

(a) providing a $\gamma\Psi\delta'$ complex;

(b) combining the $\gamma\Psi\delta'$ complex with $\tau$ under conditions effective to form $\gamma\tau\Psi\delta'$ complex; and (c) combining the $\gamma\tau\Psi\delta'$ complex with $\alpha$, $\epsilon$, $\theta$, $\delta$, and $\chi$ in any order under conditions effective to form the polymerase III* subassembly.

The $\gamma\tau\Psi\delta'$ complex can be combined with $\chi$ and $\delta$ to form a $\gamma\tau\chi\Psi\delta\delta'$ complex, which is combined with the core complex $\alpha\epsilon\theta$ or its components subunits to form the polymerase III* subassembly.

The process further comprises combining the polymerase III* subassembly with $\beta$ to form the polymerase III holoenzyme.

Pol III* Reconstitution Process G

Another embodiment of the present invention relates to a process for reconstituting the polymerase III* subassembly of E. coli DNA polymerase III holoenzyme by:

(a) providing a $\tau\Psi\delta'$ complex;

(b) combining the $\tau\Psi\delta'$ complex with $\gamma$ under conditions effective to form a $\gamma\tau\Psi\delta'$ complex; and (c) combining the $\gamma\tau\Psi\delta'$ complex with $\alpha$, $\epsilon$, $\theta$, $\delta$, and $\chi$ in any order under conditions effective to form the polymerase III* subassembly.

The process further comprises combining the polymerase III* subassembly with $\beta$ to form the polymerase III holoenzyme.

The $\gamma\tau\Psi\delta'$ complex can be formed by combining the $\gamma\Psi\delta'$ complex with $\tau$ or the $\tau\Psi\delta'$ complex with $\delta$. The $\gamma\tau\Psi\delta'$ complex can be combined with $\alpha$, $\epsilon$, $\theta$, $\chi$, and $\delta$ in any order under conditions effective to form the polymerase III* subassembly.

Reconstitution Processes for Other Subassemblies

The present invention also relates to a process for reconstituting the $\gamma$-less Pol III* subassembly from subunits $\tau$, $\alpha$, $\epsilon$, $\theta$, $\delta$, $\delta'$, $\chi$ and $\Psi$ by: combining $\tau$, $\alpha$, $\epsilon$, $\theta$, $\delta$, $\delta'$, $\chi$ and $\Psi$ in any order under conditions effective to form the $\gamma$-less Pol III* subassembly. Alternatively, $\tau$, $\chi$, and $\Psi$ can be combined to form a $\tau\chi\Psi$ complex, which can be combined with $\delta$ and $\delta'$ to form a $\tau\chi\Psi\delta\delta'$ complex. In another sequence, the $\tau\chi\Psi\delta\delta'$ complex can be formed by combining $\tau\chi\Psi\delta\delta'$ complex with $\tau$.

Another aspect of the present invention pertains to a process for reconstituting an $\alpha\tau\chi\Psi\delta\delta'$ subassembly from subunits $\tau$, $\alpha$, $\delta$, $\delta'$, $\chi$, and $\Psi$ by: combining $\tau$, $\alpha$, $\delta$, $\delta'$, $\chi$, and $\Psi$ in any order under conditions effective to form the $\alpha\tau\chi\Psi\delta\delta'$ subassembly. Alternatively, $\tau$, $\chi$, $\Psi$, $\delta$, and $\delta'$ can be combined to form a $\tau\chi\Psi\delta\delta'$ complex, which is combined with subunit $\alpha$.

Still another aspect of the present invention pertains to a process for reconstituting an $\alpha\tau\delta\delta'$ subassembly from $\tau$, $\alpha$, $\delta$, and $\delta'$ by: combining $\tau$, $\alpha$, $\delta$, and $\delta'$ in any order under conditions effective to form the $\alpha\tau\delta\delta'$ subassembly. A $\tau\delta\delta'$ complex can be first formed, then combined with $\alpha$.

The present invention also relates to a process for reconstituting an $\alpha\epsilon\theta\tau\delta\delta'$ subassembly from $\tau$, $\alpha$, $\epsilon$, $\theta\delta$, and $\delta'$ by: combining $\tau$, $\alpha$, $\epsilon$, $\theta$, $\delta$, and $\delta'$ in any order under conditions effective to form the $\alpha\epsilon\theta\tau\delta\delta'$ subassembly. A $\tau\delta\delta'$ complex formed from its component subunits can be combined with. $\alpha$, $\epsilon$, and $\theta$.

Figure 2A:
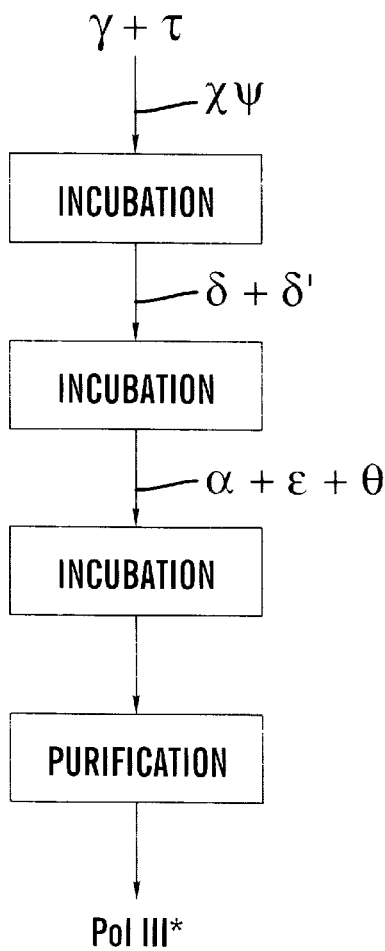
FIG. 2 is a schematic representation of two general methods, in accordance with the invention, for reconstituting Pol III*.
Figure 2B:
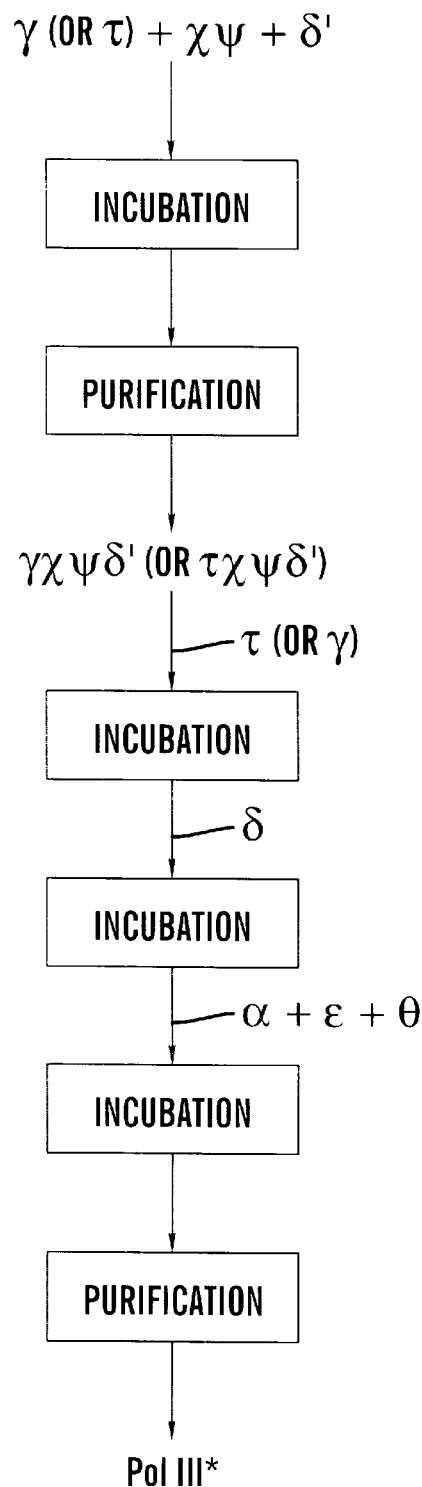
Figure 3A:
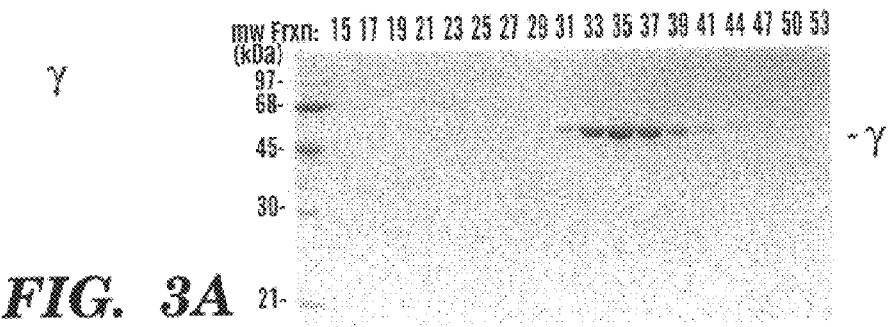
FIG. 3 depicts a gel filtration analysis of mixtures of subunits $\gamma$ and $\tau$ to determine the extent of their reactivity with one another.
Figure 3B:
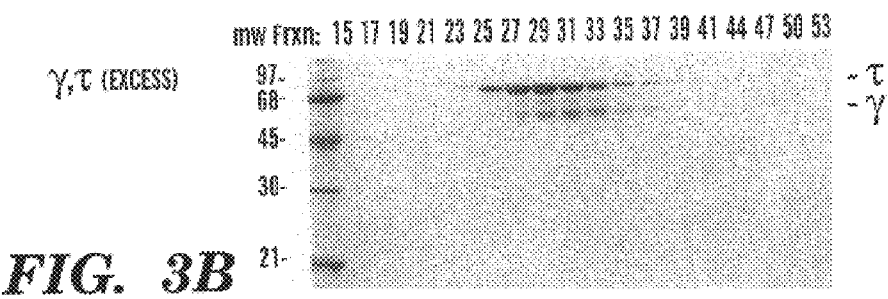
Figure 3C:
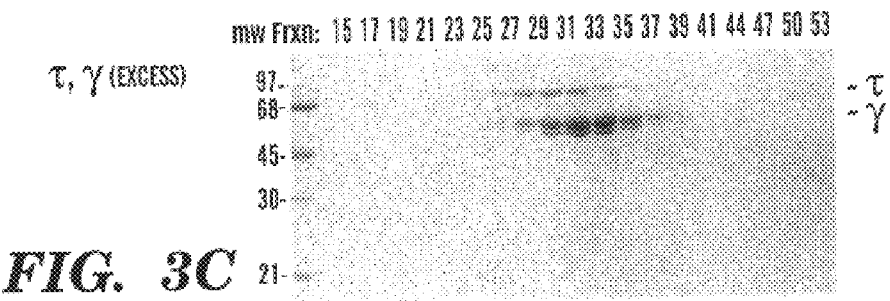
Figure 3D:
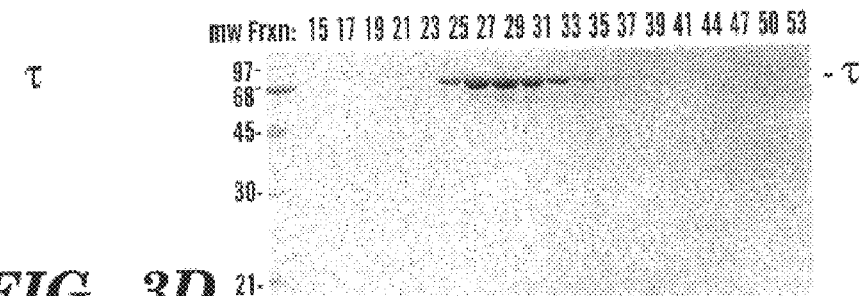
Figure 3E:

The process of the present invention provides for the reconstitution of Pol III* and other Pol III subassemblies from substantially pure peptide subunits. FIG. 2 depicts two general schemes (Methods 1 and 2) by which Pol III* can be assembled. In Method 1, $\gamma$ and $\tau$ are premixed before addition of $\delta$ and $\delta'$. In Method 2, $\delta'$ is first assembled onto $\gamma$ (or $\tau$); then the excess $\delta'$ is removed before adding $\tau$ (or $\gamma$) so that the $\gamma$-$\tau$ interaction is productive, following which $\delta$ is added.

Variations in these general assembly schemes are possible. For example, in Method 1, the $\chi\Psi$ complex and $\alpha\epsilon\theta$ core complex can be added to $\gamma$ and/or $\tau$ before or after mixing $\gamma$ with $\tau$. In Method 2, $\chi$ (or $\chi\Psi$) must be added initially to stabilize association of $\delta'$ with $\gamma$ (or $\tau$), but $\tau$ and core can be added at any point in the scheme. Possible variations of Method 1 include: 1a) placing $\chi\Psi$ on both $\gamma$ and $\tau$ before mixing them (as in FIG. 2), 1b) mixing pure $\gamma\chi\Psi$ complex with $\tau$ (this may direct the assembly of $\delta'$ to $\gamma\chi\Psi$), and 1c) mixing pure $\gamma\chi\Psi$ complex with $\gamma$ (this may direct assembly of $\delta'$ to $\tau\chi\Psi$). Possible variations of Method 2 include: 2a) starting with $\gamma\chi\Psi\delta'$ (as in FIG. 2; this may direct $\delta$ to $\gamma$), and 2b) starting with $\tau\chi\Psi\delta'$ (this may direct $\delta$ to $\tau$). Methods 1b and 2a may be expected to direct $\delta\delta'\chi\Psi$ onto $\gamma$, and Methods 1c and 2b should direct $\delta\delta'\chi\Psi$ onto $\tau$. Method 1 is a preferred embodiment of the invention, variation 1a being especially preferred.

The various Pol III* preparations were compared for differences in their activity with $\beta$ on singly primed ssDNA and for differences in their subunit stoichiometry. They were all within 2-fold of the activity of purified natural Pol III*, and they all had the same subunit composition, as determined by scanning of Coomassie Blue stained SDS polyacrylamide gels.

In the process of the invention, using either method, the "outer" subunits such as $\chi$ and $\theta$ are added in excess over subunits more central to the structure such that all complexes are driven to completion. The $\tau$ subunit is the most central since it binds both the $\gamma$ complex and core, and therefore $\tau$ must be limiting in the assembly scheme. The $\gamma$-$\tau$ interaction appears to be an equilibrium that needs to be pushed by a 3-fold ]excess of $\gamma$ to make all the $\tau$ bind $\gamma$, and the excess $\gamma$ complex that results is difficult to separate from Pol III*. However, if insufficient $\gamma$ is used to push this equilibrium then an 8-subunit form of Pol III assembles which has all the subunits except for $\gamma$ (referred to below as "$\gamma$-less Pol III*"). It is desirable to reduce the amount of $\gamma$-less Pol III*, even at the expense of forming excess $\gamma$ complex, since it is difficult to separate $\gamma$-less Pol III* from Pol III*.

In accordance with Method. 1 of the process of the present invention, the following molar ratios of subunits and complexes are preferably employed: $\gamma$ to $\tau$ (based on $\gamma$ and $\tau$ as dimers, all other subunits and complexes as monomers), about 1:1 to 5:1, more preferably about 1.5:1 to 3:i; $\chi$ to $\tau$ and $\Psi$ to $\tau$, each about 2:1 to 10:1, more preferably, about 4:1 to 7:1; $\delta$ to $\tau$ and $\delta'$ to $\tau$, each about 2:1 to 10:1, more preferably about 4:1 to 6:1; $\alpha$ to $\tau$, about 1:1 to 5:1, more preferably about 2:1 to 3:1; $\epsilon$ to $\tau$ and $\theta$ to $\tau$, each about 2:1 to 10:1, more preferably about 3:1 to 5:1 for $\epsilon$:$\tau$ and about 4:1 to 7:1 for $\theta$:$\tau$; $\tau\chi\Psi$ complex to $\gamma$, about 0.1:1 to 1:1; $\gamma\chi\Psi$ complex to $\tau$, about 1:1 to 10:1.

For Method 2 of the process of the present invention, the following molar ratios of subunits and complexes are preferably utilized γχΨδ' complex to τ, about 1:1 to 10:1; τχΨδ' complex to γ, about 0.1:1 to 1:1.

In accordance with the process of the invention, the aqueous compositions comprising subunits and complexes are incubated preferably for a time period of about 5 minutes to 120 minutes at a temperature of about 0° C. to 45° C., more preferably for about 15 minutes to 60 minutes at about 10° C. to 20° C.

EXAMPLES

The following materials and general procedures were employed as described in detail below:

Materials—Radioactive nucleotides were obtained from Dupont-New England Nuclear, and unlabeled nucleotides were obtained from Pharmacia-LKB. Proteins were purified as described: α, ε, γ, and τ in Studwell and O'Donnell, 1990, *J. Biol Chem.*, vol. 265, pp 1171–1178; β in Kong et al., 1992, *Cell*, vol. 69, pp 425–437; δ and δ' in Dong et al., 1993, *J. Biol. Chem.*, vol. 268, pp 11758–11765; χ and Ψ in Xiao et al., 1993, *J. Biol. Chem.*, vol. 268, pp 11773–11778; 0 in Studwell-Vaughn and O'Donnell, 1993, *J. Biol. Chem.* vol. 268, pp 11785–11791; naturally purified Pol III* in Maki et al., 1988, *J. Biol. Chem.*, vol. 263, pp 6570–6578, and γ complex in Maki and Kornberg, 1988, *J. Biol. Chem.* vol. 263, pp 6555–6560; these disclosures are incorporated herein by reference. Protein concentrations were determined from their extinction coefficients at 280 nm except for Pol III* and γ complex purified without overproduction, which were determined using the Coomassie Blue based protein stain from BioRad using bovine serum albumin (BSA) as a standard. M13mp18 ssDNA was phenol extracted from-phage which was purified by two consecutive bandings (first down and then up) in cesium chloride gradients. M13mp19 ssDNA was primed with a DNA 30mer (map position 6817–6846) as described in Studwell and O'Donnell, 1990, *J. Biol. Chem.*, vol. 265, pp 1171–1178. DNA oligonucleotices were purchased from Oligos etc. Replication buffer is 20 mM Tris-HCl (pH 7.5), 4% glycerol, 0.1 mM EDTA, 40 μg/ml BSA, 5 mM DTT, 8 mM MgCl$_2$, 0.5 mM ATP, 60 μM dCTP, 60. μM dGTP, 60 μM dATP and 20 μM [α-$^{32}$P]TTP (specific activity 2000–8000 cpm/pmol). Gel filtration buffer is 20 mM Tris-HCl (pH 7.5), 10% glycerol, 2 mM DTT, 0.1 mM EDTA, and 100 mM NaCl. SPR buffer is 10 mM Hepes-HCl (pH 7.4), 150 mM NaCl 3.4 mM EDTA. Sedimentation buffer is 20 mM Tris-HCl (pH 7.5), 2 mM DTT, 0.1 mM EDTA, and 100 mM NaCl. Reconstitution buffer is 20 mM Tris-HCI (pH 7.5), 2 mM DTT, 0.1 mM EDTA, 10% glycerol.

Replication assays—Replication assays contained 63 ng (32 fmol) singly primed M13mp18 ssDNA, 0.82 μg SSB, 8.8 ng (56 fmol) αε, and 20 ng (246 fmol) β$_2$ in a final volume of 25 μl (after the addition of the remaining proteins). All proteins were added to the assay on ice, then shifted to 37° C. for 5 minutes. DNA synthesis was quenched and quantitated using DE81 paper as described in Stukenberg et al., 1991, *J. Biol. Chem.*, vol. 266, pp 11328–11334, the disclosures of which are incorporated herein by reference. When needed, proteins were diluted in 20 mM Tris-HCl (pH 7.5), 2 mM DTT, 0.5 mM EDTA, 20% glycerol and 50 μg/ml BSA.

Preparation of reconstituted complexes—Proteins were incubated in reconstitution buffer for 30 min. at 15° C. unless stated otherwise. The concentrations of all subunits except τ and γ are expressed as monomer. The concentrations of γ and τ are expressed as dimer since this is their final aggregation state when assembled with the other subunits.

Buffers used for ion exchange chromatography were either Buffer A (20 mM Tris-HCl (pH 7.5), 2 mM DTT, 0.5 mM EDTA, 10% glycerol), or Buffer B (20 mM Hepes-OH (pH 7.5), 2 mM DTT, 0.5 mM EDTA and 10% glycerol).

The following examples further illustrate the invention:

EXAMPLE 1

Preparation and Gel Filtration of Reconstituted γ And τ Complexes

Gel filtration of reconstituted complex γ and τ complex was performed using an HR 10/30 Superose 6 (Pharmacia, LKB) column equilibrated in column buffer containing 5 mM MgCl$_2$ and 0.2 mM ATP. The γ (78μg, 0.88 nmol as dimer) or τ subunit (118 μg, 0.83 nmol as dimer) was incubated with χ (39 μg, 2.4 nmol as monomer) and Ψ (30 μg, 2 nmol as monomer) for 30 minutes at 15° C. To this protein mix was added δ (77 μg, 2 nmol as monomer) and δ' (74 μg, 2 nmol as monomer) for 30 minutes at 15° C. This protein mix was then concentrated to 100 μl by centricon 30 spin dialysis (Amicon) and gel filtered. After the first 7 ml, fractions of 200 μl were collected, followed by analysis in 15% SDS polyacrylamide gels (100 μl per lane) stained with Coomassie Blue R-250. Densitometry of stained gels was performed using a Pharmacia-LKB Ultrascan XL laser densitometer. Replication assays of column fractions were performed by first diluting a 2 μl aliquot 20-fold and then adding 2 μl to the assay.

Mixtures of three and four of the subunits that are contained in the γ complex were incubated for 30 minutes at 15° in 200 μl column buffer and contained (when present): γ, 84 μg (0.9 nmol as dimer); δ, 57 μg (1.5 nmol); δ, 56 μg (1.56 nmol), χ, 41.8 μg (2.52 nmol), Ψ, 25μg (1.67 nmol). Subunit mixtures were gel filtered on an HR 10/30 Superose 12 column equilibrated in column buffer as described above except that, after the first 6.0 ml of buffer, fractions of 170 μl were collected. Additions of Ψ in the absence of τ required 0.5 M urea as described in Kelman and O'Donnell, 1994, *Current Opinion in Genetics and Development*, vol. 4, pp 185–195, the disclosures of which are incorporated herein by reference. To avoid urea, mixtures containing both χ and Ψ were assembled using χΨ complex (68 μg, 2.14 nmol) in which the urea was dialyzed away. Protein standards (BioRad and Sigma) were a mixture of 50 μg each in 100 μl column buffer. The K$_{av}$ was calculated using the equation: K$_{av}$=(V$_e$−V$_o$)/(V$_t$−V$_o$); where V$_e$ is the observed elution volume, V$_t$ is the included volume, and V$_o$ is the exclusion volume. V$_t$ for both Superose 6 and 12 columns was 24 ml (manufacturer's specifications) and the V$_o$, determined using M13mp18 ssDNA saturated with SSB (total mw≈25 Mda), was 6.0 ml for Superose 12 and 7.0 ml for Superose 6.

EXAMPLE 2

Preparation of Reconstituted γ Complex

A mixture of 11.1 μg γ (118 nmoles as dimer), 13.7 μg δ (355 nmoles as monomer), 8.7 μg δ' (235 nmoles as monomer), 5.9 μg χ (354 nmoles as monomer) and 3.6 μg Ψ (237 nmoles as monomer in 4 M urea) was incubated in a final volume of 63.75 ml buffer A for 30 minutes at 15° C. (incubation was started with χ and Ψ proteins combined together in a final volume sufficient to bring the urea concentration to 0.5 M; then the other subunits were added). This mixture was loaded onto an 8 ml Mono Q HR 10/10 column (Pharmacia-LKB) and eluted with a 180 ml linear gradient of 0–0.4 M NaCl in buffer A at 0.3 ml/min. Sixty-six fractions of 2.5 ml each were collected. Fractions 46–52, which contained homogenous $\gamma\delta\delta'\chi\Psi$, were pooled (18.5 ml, 18 mg) and dialyzed against 4 liters of buffer A to a conductivity equal to 30 mM NaCl.

EXAMPLE 3

Preparation of Reconstituted pol III Core

A mixture of 10 mg (78 nmol) $\alpha$, 6.4 mg (229 nmol) $\epsilon$, and 6 mg (698 nmol) $\theta$ was incubated in a volume of 7.4 ml then chromatographed on a Mono Q HR 5/5 column eluted with a 32 ml linear gradient of 0–0.4 M NaCl in Buffer A. Fractions of 0.5 ml were collected and analyzed in a Coomassie Blue stained SDS polyacrylamide gel. The core polymerase eluted at approximately 0.25 M NaCl (11 mg final).

EXAMPLE 4

Preparation of $\gamma\delta'\chi\Psi$ Complex

The $\gamma\delta'\chi\Psi$ complex was made in two steps; first $\gamma\chi\Psi$ complex was constituted and purified as described in Dong, and O'Donnell, 1993, *J. Biol. Chem.*, vol. 268, pp 11773–11778, the disclosures of which are incorporated herein by reference. Then $\delta'$ was added, and the resulting $\gamma\delta'\chi\Psi$ complex was purified (Alternatively, the $\gamma\delta'\chi\Psi$ complex can be made by mixing all four subunits followed by purification on Mono Q). The $\gamma\chi\Psi$ complex (1.5 mg, 52.5 nmol) was incubated with $\delta'$ (3.89 mg, 105 nmol) in 3.06 ml and then the mixture was chromatographed on a Mono Q HR 5/5 column equilibrated in buffer A. The $\gamma\delta'\chi\Psi$ complex was eluted from the column with a 32 ml linear gradient of 0–0.4 M NaCl in Buffer A. The $\gamma\delta'\chi\Psi$ complex elutes last at approximately 0.28 M NaCl. Column fractions containing $\gamma\delta'\chi\Psi$ were pooled (4.2 mg in 3 ml) and stored at −70° C.

EXAMPLE 5

Preparation of Reconstituted pol III' Complex

Pol III' was assembled and purified several times during this study, but the method was similar in that the same molar ratios of subunits was used, just the total amounts differed. In general, Pol III' was constituted by mixing $\alpha$, $\epsilon$, $\theta$ and $\tau_2$ at molar ratios of 3:4.5:6.75:1, respectively (molarity of $\tau$ as dimer, the rest as monomer) in reconstitution buffer and incubated for 30 minutes at 15° C. Constituted Pol III' was concentrated to 100 $\mu$l by spin dialysis using Centricon 3D and isolated by gel filtration on a Superose 6 column to remove excess core, $\epsilon\theta$ complex and $\theta$ subunit.

EXAMPLE 6

Preparation of Reconstituted $\gamma$-Less pol III* Subassembly

Pol III* lacking $\gamma$ was constituted upon incubating $\tau$ (239 $\mu$g, 0.84 nmol as dimer), $\chi$ (40.5 $\mu$g, 2.44 nmol), and $\Psi$ (30 $\mu$g, 1.97 nmol, in 6 $\mu$l of 4 M urea) in a final volume of 98.1 $\mu$l after which $\delta$ (92 $\mu$g, 2.38 nmol) and $\delta'$ (73.7 mg, 1.99 nmol) were added. This mixture was further incubated 30 minutes at 15° C., at which time $\alpha$ (239 $\mu$g, 1.99 nmol), $\epsilon$ (67.6 $\mu$g, 2.46 nmol) and $\theta$ (24.13 $\mu$g, 2.8 nmol) were added to a final volume of 260 $\mu$l containing 5 mM $MgCl_2$ and 0.2 mM ATP. This mixture was further incubated 30 minutes at 15° C. and then concentrated to 100 $\mu$l at 4° C. with a Centricon 30 (Amicon) followed by purification through gel filtration on a Superose 6 column.

The $\gamma$-less Pol III* has a Stokes radius of 97Å and an approximate mass of 1 mDa when compared with protein standards. Densitometry analysis of a Coomassie Blue stained gel yielded a subunit molar ratio (after correcting for differences in Coomassie Blue staining for each subunit) of: $\alpha_{3.0}\epsilon_{2.7}\theta_{ND}\tau_{4.0}\delta_{0.7}\delta'_{0.7}\chi_{0.5}\Psi_{1.0}$. The size and stoichiometry of $\gamma$-less Pol III* is most consistent with a particle composition of $\alpha_4\epsilon_4\theta_4\tau_4\delta_1\delta'_1\chi_1\Psi_1$ and a calculated mass of 1,050 kDa It is proposed that the $\tau$ subunit is a tetramer with four core polymerases and one subunit each of $\delta$, $\delta'$, $\chi$ and $\Psi$. This structure is similar to the structure of Pol III*, except for having a $\tau$ tetramer instead of a heterotramer of $\tau_2\tau_2$ for Pol III*, for which only two $\alpha\epsilon\theta$ complexes are able to bind to the $\tau$ dimer. Consistent with four core polymerases within $\gamma$-less Pol III*, its specific activity is 2.2-fold higher than naturally purified Pol III* and 1.45-fold higher that reconstituted Pol III* (4.9 pmol/mg protein/minute).

EXAMPLE 7

Interaction of $\gamma$ With $\tau$

The initial observation that Pol III' and $\gamma$ complex did not assemble into Pol III* implied that perhaps extra subunits needed to be added For example, perhaps the $\gamma$ complex assembles with the $\gamma$-less Pol III* to form a dimeric polymerase with $\gamma$ complex and a $\tau$ complex. However, this was found not to occur. It was then assumed that one of the subunits of either Pol III' or the $\gamma$ complex was preventing assembly of Pol III*, this assumption proved to be correct.

The approach was to mix combinations of two subunits, one from Pol III' and one from the $\gamma$ complex, and assay for an interaction by gel filtration. Using this approach a contact of $\gamma$ with $\tau$ was identified (FIG. 3), however, none of the other subunits of Pol III' (i.e. $\alpha\epsilon\theta$) bound to any subunit of $\gamma$ complex. The $\gamma$-$\tau$ complex is somewhat difficult to observe by gel filtration because alone they each migrate as a higher order oligomer, consistent with a tetrameric state (Studwell-Vaughan and O'Donnell, 1991, *J. Biol. Chem.*, vol. 266, pp 19833–19841; Tsuchihashi and Kornberg, 1989, *J. Biol. Chem.*, vol. 264, pp 17790–17795, the disclosures of which are incorporated herein by reference), but upon mixing them they migrate as a $\tau_2\gamma_2$ heterotramer. The $\tau_2\gamma_2$ heterotramer elutes earlier than $\gamma$ alone but slower than $\tau$ alone. A study of the $\gamma$-$\tau$ interaction is presented in FIG. 3. Panel A shows the $\gamma$ subunit alone, and Panel D shows $\tau$ alone. Panel B shows the result of mixing $\gamma$ with a 4-fold excess of $\tau$. Comparison of the $\gamma$ position in Panel B with $\gamma$ alone in Panel A shows that $\tau$ causes $\gamma$ to elute earlier than $\gamma$ alone (compare fractions 27–33 in Panel B to fractions 33–37 in Panel A). When $\gamma$ is in a 4-fold excess over $\tau$ (Panel C), it causes $\tau$ to elute later (smaller) than $\tau$ alone (fractions 29–33 in Panel $\chi$ relative to fractions 27–31 in Panel D).

The observation of $\gamma$ and $\tau$ forming a mixed oligomer is not surprising as $\gamma$ and $\tau$ are related, $\tau$ contains the $\gamma$ sequence plus an additional 24 kDa of protein at the C-terminus. Since they oligomerize it is reasonable to expect them to form a heteroligomer. The formation of the $\gamma_2\tau_2$ complex does not appear to be disproportionately favored relative to homotetramer formation as an equimolar mixture of $\gamma$ and $\tau$ does not yield a heterotramer as the sole product (FIG. 3, Panel E). The positions of $\tau$ and $\gamma$ are both affected but they do not fully comigrate indicating presence of all three tetramers: $\tau_4$, $\gamma_4$ and $\gamma_2\tau_2$.

EXAMPLE 8

Chemical Crosslinking of Subunits $\gamma$ and $\tau$

Solutions of either 400 pM $\gamma$, 400 pM $\tau$ or a mixture of 200 pM each of $\gamma$ and $\tau$ were incubated at 15° C. for 30 minutes in 80 µl of 60 mM sodium phosphate (pH 7.0), 1 mM EDTA, 10% glycerol, and either 0.1, 0.3, 0.5, 1 or 2 M NaCl. The solutions were shifted to 25° C. and 8 µl of dimethyl suberimidate (DMS) at 11 mg/ml in the same buffer (but at pH 10) was added. After 30 minutes at 25° C., the reactions were quenched upon adding 8 µl M glycine and analyzed by electrophoresis on a 8% SDS polyacrylamide gel.

Figure 4:
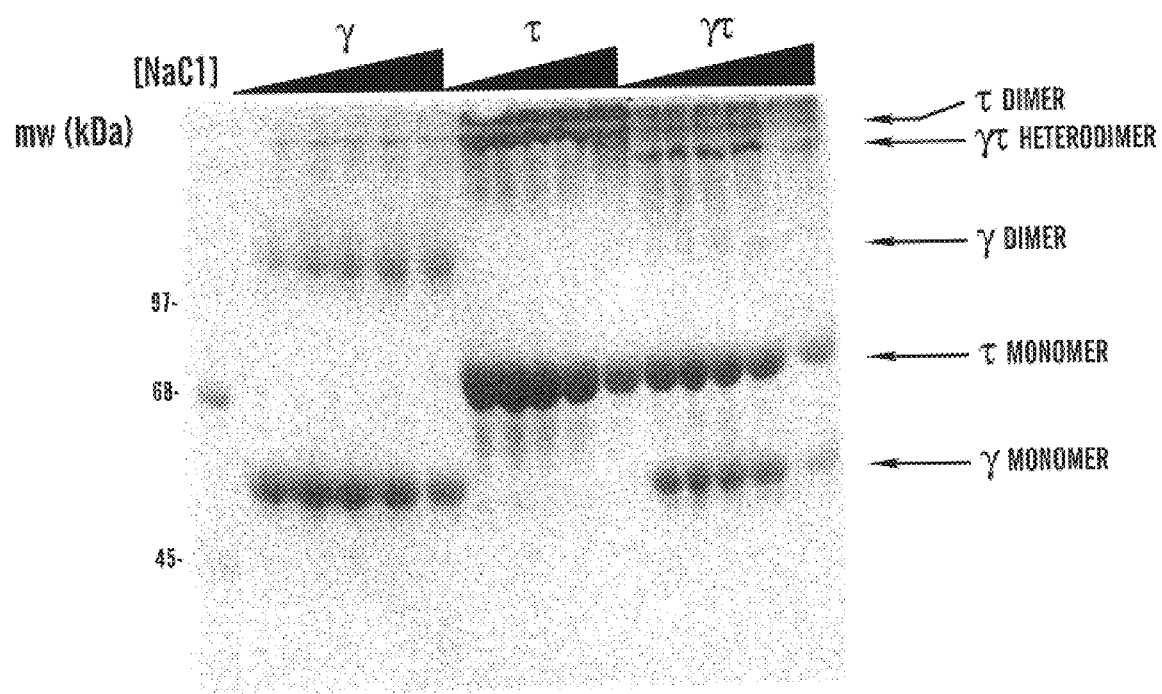
FIG. 4 shows a gel filtration analysis of chemically crosslinked $\gamma$ and $\tau$.
Figure 5A:
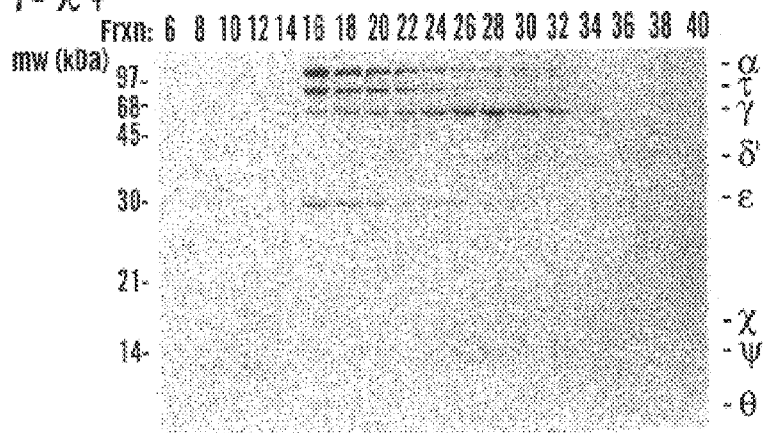
FIG. 5 depicts a gel filtration analysis showing the inhibition of the interaction of $\gamma$ with $\tau$ by the $\delta$ subunit.
Figure 5B:
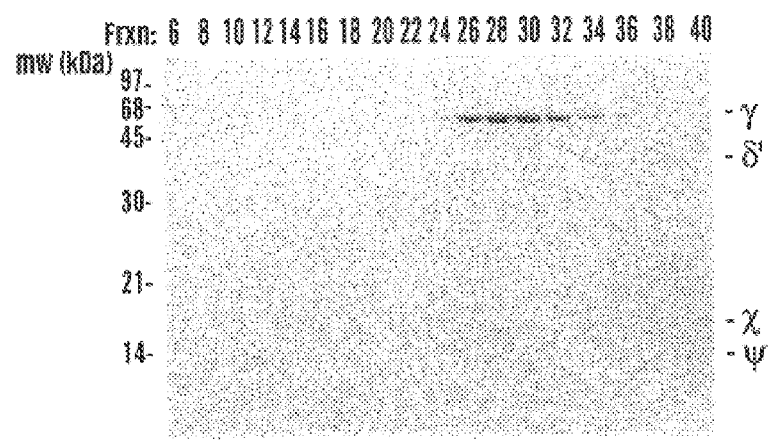
Figure 5C:
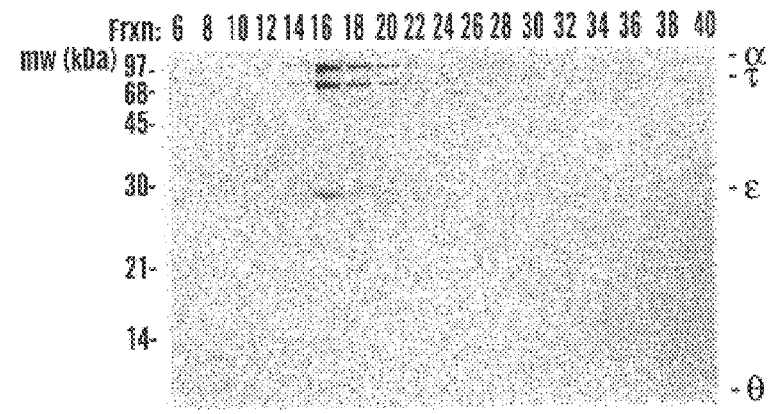
Figure 5D:
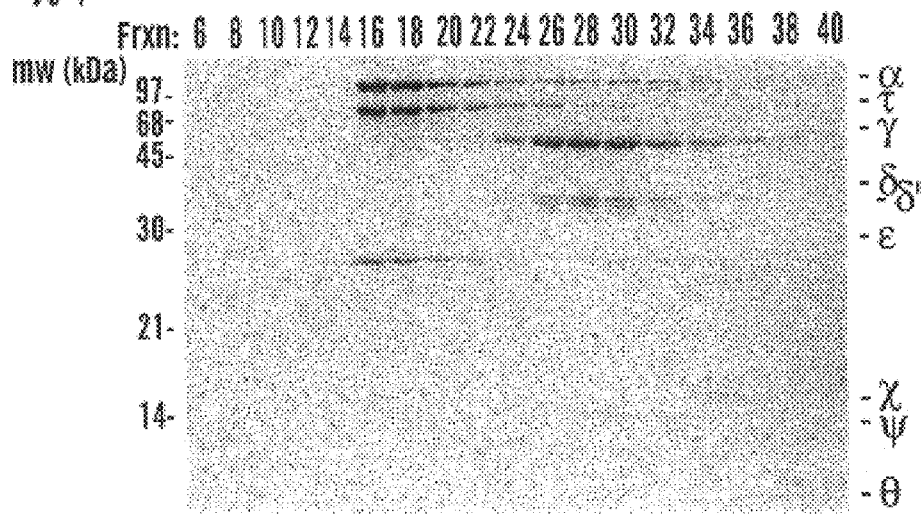
Figure 5E:

In FIG. 4 the interaction between $\gamma$ and $\tau$ is shown by chemical crosslinking. Lanes 2–6 show crosslinking of $\gamma$ at increasing concentrations of NaCl. The $\gamma$ monomer and dimer are clearly visible, the trimer and tetramer forms are present, but on the gel of FIG. 9 they are unresolved at the top. Lanes 7–11 show crosslinking of $\tau$ and again at all salt concentrations the $\tau$ monomer and dimer forms are evident, and higher states are unresolved at the top. The last five lanes show crosslinking of an equimolar mixture of $\gamma$ and $\tau$. The band indicated by the arrow is unique to the $\gamma$, $\tau$ mixture and the presumed $\gamma$-$\tau$ complex migrates between the $\gamma_2$ and $\tau_2$ positions. The presence of both $\gamma$ and $\tau$ in this crosslinked band has been confirmed using either $^3$H-$\gamma$ or $^3$H-$\tau$ with the result that $^3$H label is present in this position regardless of which subunit is labeled.

EXAMPLE 9

Inhibition of Interaction of $\gamma$ With $\tau$ By $\delta$

The assumption that a subunit of $\gamma$ complex or Pol III' prevents their association into Pol III* led to the identification of the $\gamma$-$\tau$ interaction, as described in Example 7 above. Binding of $\alpha$, $\alpha\epsilon$ complex, or the entire $\alpha\epsilon\theta$ core polymerase to $\tau$ before (or after) the addition of $\gamma$, was found not to inhibit formation of the $\tau$-$\gamma$ complex. Likewise, prior formation of $\gamma\Psi$, $\gamma\chi\Psi$ and $\gamma\delta'\chi\Psi$ did not prevent interaction with $\tau$ (or Pol III'). Hence, by exclusion it appears that $\delta$ is the subunit responsible for inhibiting the interaction of $\gamma$ with $\tau$. The $\delta$ subunit does not stably interact with $\gamma$ in the absence of $\delta'$ and thus the smallest complex that can be used to test the prediction is the $\gamma\delta\delta'$ complex. As expected, the $\gamma\delta\delta'$ complex did not bind to Pol III', implying that $\delta$ indeed prevents interaction between Pol III' and the $\gamma$ complex. FIG. 5 illustrates the finding that the presence of $\delta$ prevents association of Pol III' and the $\gamma\delta'\chi\Psi$ complex, but if $\delta$ is added last, these complexes assemble with $\delta$ into Pol III*.

Panel A of FIG. 5 depicts the results from a mixture of Pol III' with a 3-fold molar excess of the $\gamma\delta'\chi\Psi$ complex; some of the $\gamma\delta'\chi\Psi$ complex binds to and comigrates with Pol III' (in fractions 16–20). The $\gamma\delta'\chi\Psi$ complex alone (Panel B) migrates much later (fractions 26–32) and is well resolved from Pol III' (Panel C, fractions 16–20).

In Panel D are shown the results obtained when the $\gamma$ complex is mixed with Pol III'; the filtration analysis shows they do not associate, as described more fully in FIG. 1. Panel E illustrates the results when the $\delta$ subunit has been withheld until after $\gamma\delta'\chi\Psi$ and Pol III' have been given time to associate. Then $\delta$ is added and the filtration analysis shows that Pol III* has formed. Thus, the binding of $\delta$ to $\gamma\delta'\chi\Psi$ prevents interaction with Pol III', presumably by interfering with the $\gamma$-to-$\tau$ contact.

EXAMPLE 10

Figure 6A:
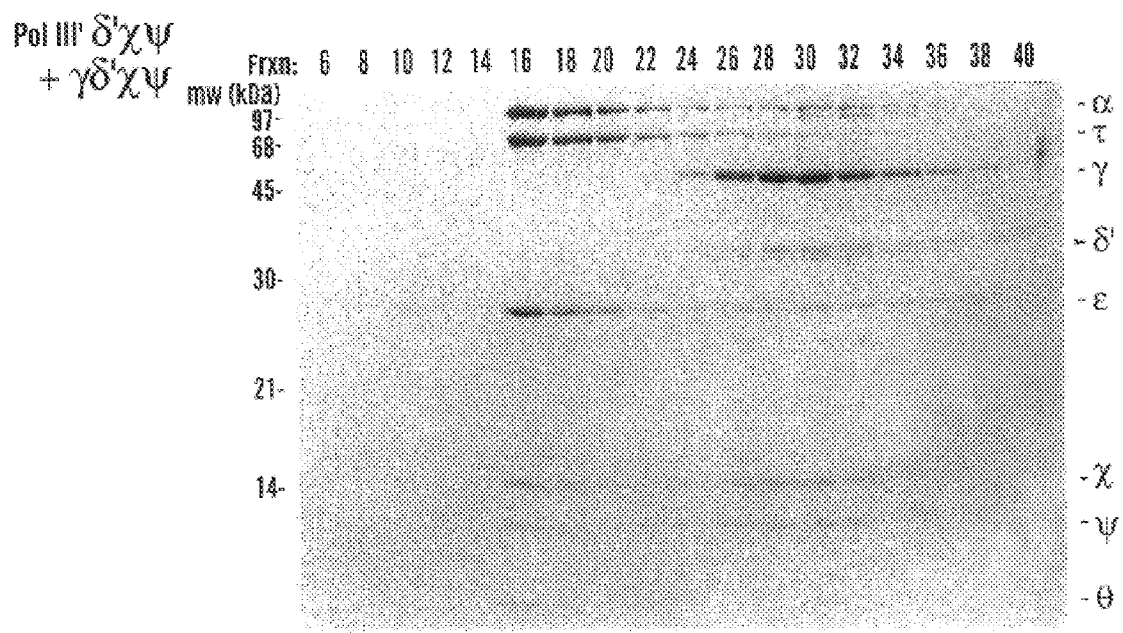
FIG. 6 depicts a gel filtration analysis showing that $\delta'$ bound to both $\gamma$ and $\tau$ inhibits the interaction of $\gamma$ with $\tau$.
Figure 6B:
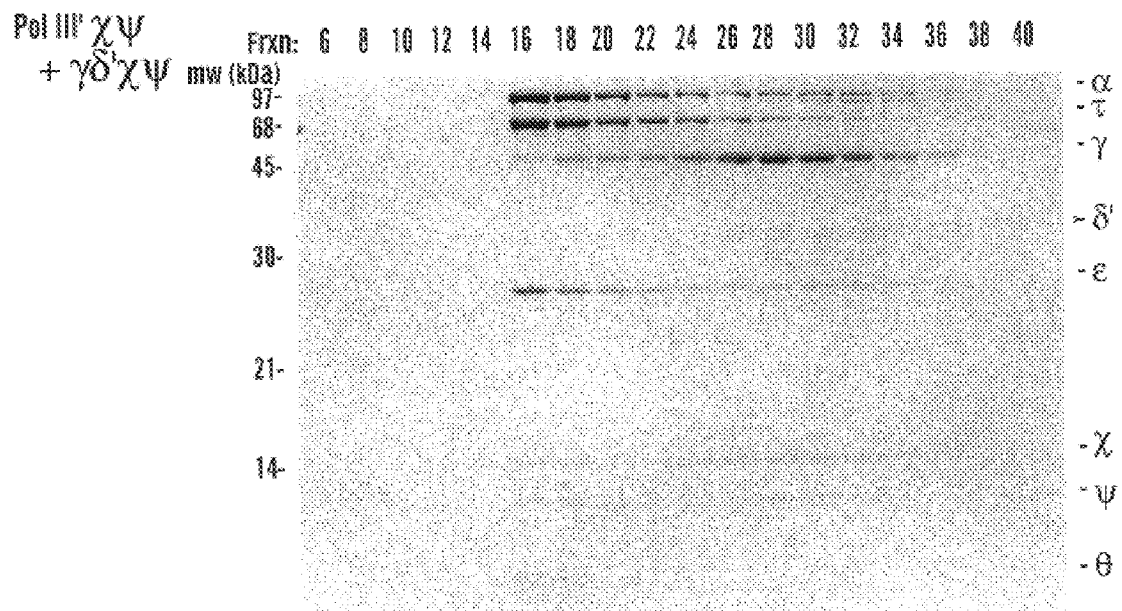

Prevention of $\gamma$-$\tau$ Interaction By $\delta'$ Bound to Both $\gamma$ And $\tau$ Both $\gamma$ and $\tau$ can bind $\delta\delta'\chi\Psi$; to determine whether both $\gamma$ complex and "$\tau$complex" clamp loaders could exist within Pol III*, an attempt was made to construct a Pol III* assembly containing both a $\tau$ complex and a $\gamma$ complex. Obviously, the $\delta$ subunit had to be excluded from the reaction until after the $\gamma$-$\tau$ contact has been formed A Pol III'-$\delta'\chi\Psi$ complex and a $\gamma\delta'\chi\Psi$ complex were assembled, and the mixture was analyzed by gel filtration (FIG. 6). The result shows that they did not interact (Panel A), as is most simply observed by examining the different peak positions of $\tau$ (fractions 16–20) and $\gamma$ (fractions 26–32). However, a Pol III'-$\chi\Psi$ complex was able to bind the $\gamma\delta'\chi\Psi$ complex (Panel B), as evidenced by some comigration of $\gamma$ with $\tau$ in fractions 16–22. Hence, even though both $\gamma$ and $\tau$ can bind $\delta'$, if $\delta'$ is on both $\gamma$ and $\tau$, $\gamma$-$\tau$ contact cannot be established, as though there is only enough room in the heterotramer for one molecule of $\delta'$. The $\delta'$ inhibition of the $\gamma$-$\tau$ contact using the minimal assemblies possible has also been confirmed; $\tau\Psi\delta'$ does not bind $\gamma\Psi\delta'$, but $\tau\Psi$ binds $\gamma\Psi\delta'$, and $\gamma\Psi$ binds $\tau\Psi\delta'$.

These results showing that $\delta'$ can be on $\gamma$ or $\tau$, but not both, is consistent with the observed stoichiometry of one $\delta'$ (and $\delta$, $\chi$ and $\Psi$) in Pol III*. Further, the single copy of $\delta$ in Pol III* follows from the fact that the $\delta\delta'$ complex is 1:1 and the point of attachment of $\delta$ to the $\gamma$ complex is through interaction with $\delta'$ (Onrust and O'Donnell, 1993, *J. Biol. Chem.*, vol. 268, pp 11766–11772, the disclosures of which are incorporated herein by reference). The fact that there is only one $\delta'$ in Pol III*, coupled with the fact that $\delta'$ stabilizes the $\gamma\chi\Psi$ complex, provides a ready explanation for why Pol III* retains only one copy of $\tau$ and $\Psi$, even though their presence on both $\gamma$ and $\tau$ does not prevent Pol III* assembly. Hence, only the subunit ($\gamma$ or $\tau$) that receives $\delta'$ will retain the $\chi\Psi$ complex due to the stabilization incurred by $\delta'$.

EXAMPLE 11

Failure of a Mixture of Pol III' and $\gamma$ Complex to Assembly into Pol III*

Figure 7A:
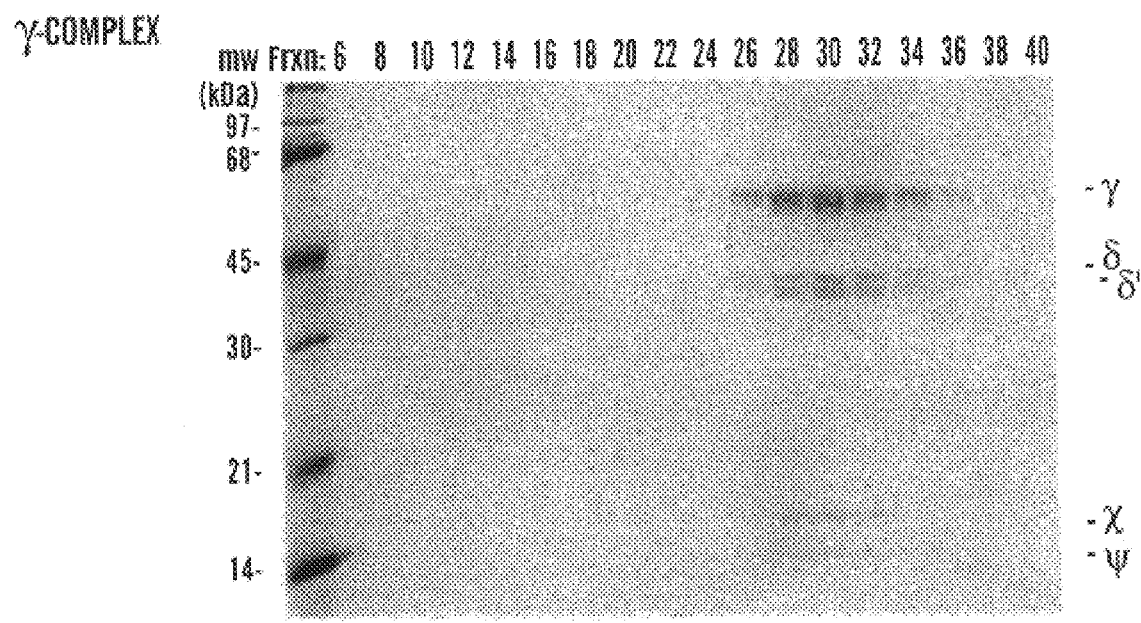
FIG. 7 depicts a gel filtration analysis of Pol III' and γ complexes that shows their failure to assemble into Pol III*.
Figure 7B:
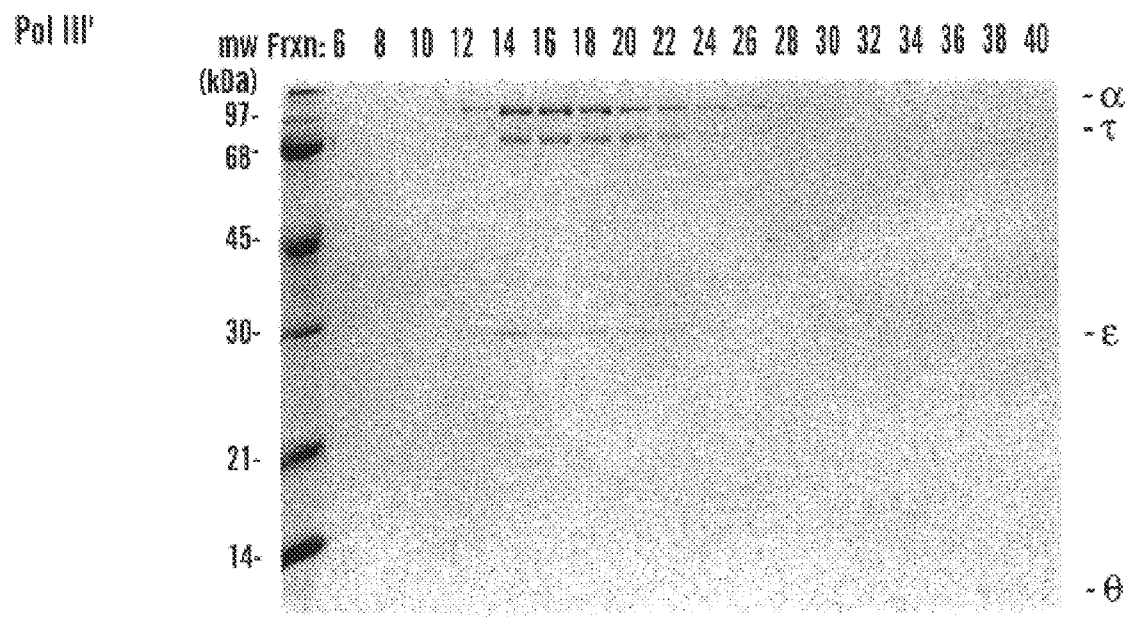
Figure 7C:
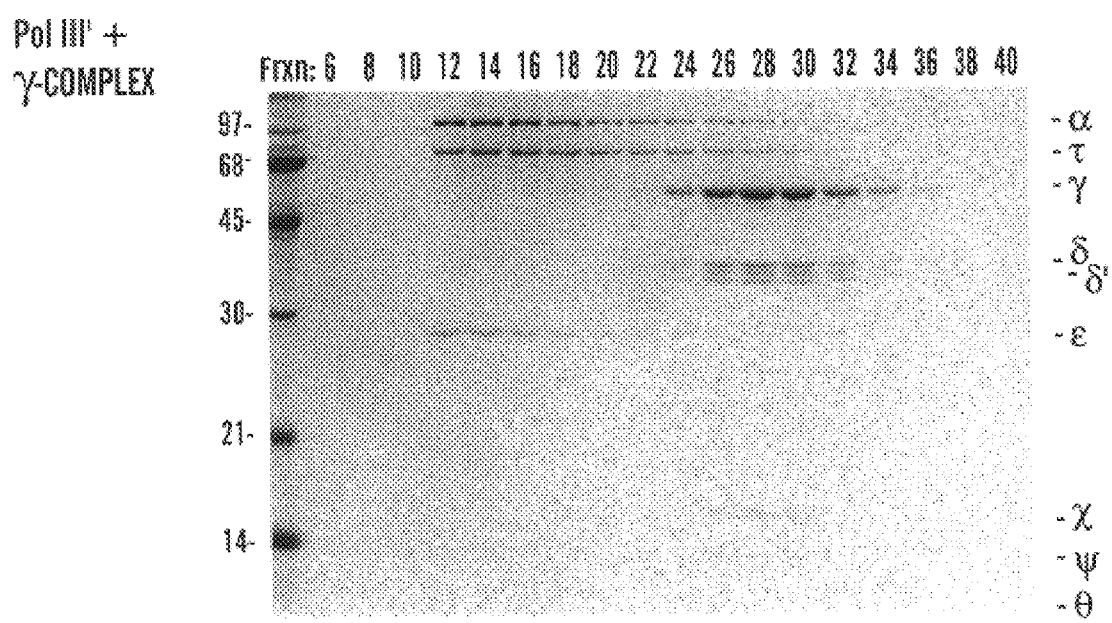

To determine whether Pol III' (($\alpha\epsilon\theta\tau)_2$) and $\gamma$ complex ($\gamma_2\delta\delta'\chi\Psi$) would assemble into Pol III*, a mixture of Pol III' and $\gamma$ complex was prepared. In replication assays, the mixture of Pol III' and $\gamma$ complex are essentially as effective in providing processive DNA synthesis with $\beta$ as the Pol III* assembly is. Hence, to assay possible formation of Pol III*, simple replication assays could not be used; following the assembly by physical methods was required. FIG. 7 depicts an assay of Pol III* assembly by gel filtration followed by Coomassie Blue staining of an SDS polyacrylamide gel of the column fractions. Panels A and B, respectively, show the analyses of the $\gamma$ complex and Pol III'. The $\gamma$ complex elutes in fractions 26–34 (Panel A) and Pol III' peaks in fractions 14–22 (Panel B). If Pol III' and $\gamma$ complex associate into Pol III*, then all nine subunits should coelute in a position earlier than either complex alone. Analysis of the mixture of Pol III' and $\gamma$ complex in Panel C shows they do not associate to a significant extent; the subunits neither comigrate nor elute earlier; instead, the Pol III' and $\gamma$ complex elute in the same positions as when analyzed separately.

Formation of Pol III* requires that the $\tau$ and $\gamma$ subunits associate with each other, and this $\gamma$-$\tau$ association does not occur when using intact Pol III' and $\gamma$ complex. The underlying reason that $\tau$ (in Pol III') cannot bind $\gamma$ in the $\gamma$ complex rests with the $\delta$ subunit, which prevents their interaction; $\delta$ needs to be added after $\gamma$ and $\tau$ have been preincubated. In fact, the $\tau$-$\gamma$ contact can be made upon incubating Pol III' with a complex of $\gamma\delta'\chi\Psi$ ($\gamma$ complex lacking $\delta$); subsequent addition of $\delta$ results in formation of Pol III*. The $\delta'$ subunit can also inhibit interaction of $\tau$ with $\gamma$, thus preventing Pol III* formation. The δ' subunit can bind both γ and τ (Ψ must also be present for δ' to bind γ or τ), but if δ' is allowed to bind both γ and τ, it prevents the essential association of γ with τ.

EXAMPLE 12

Preparation of Reconstituted pol III* Subassembly

Two general methods were used to constitute Pol III*.

Method 1—First the χΨ complex was constituted and dialyzed to remove urea in the Ψ preparation by mixing 1.414 mg (85 nmol) χ with 0.864 mg (57 nmol) Ψ in a final volume of 4.2 ml (urea was 0.7 M) for 1 hr and then dialyzed against reconstitution buffer. The τ subunit (504 µg, 3.5 nmol) was incubated 60 min. with χΨ complex (224 µg, 7 nmol) in 488 µl. The γ (1.0 mg, 10.6 nmol) subunit was incubated with χΨ complex (676 µg, 212 nmol) for 60 min. in 1.953 ml. The mixtures were then combined and incubated 1 hr, after which a 665 µl mixture of 787 µg δ' and 823 µg δ (21.3 nmol each) was added, followed by a further incubation for 30 min. During this time the core polymerase was constituted in a separate tube containing α (2.77 mg, 21.3 nmol), ε (878 µg, 31.9 nmol) and θ (412 µg, 47.9 nmol) in 5.4 ml for 1 hr. Then the core was combined with the τγδδ'χΨ mixture and incubated a further 1 hr. The mixture was then loaded onto a 4 ml Heparin Sepharose column (Pharmacia-LKB) equilibrated in Buffer A and eluted with a 40 ml linear gradient of 0–0.325 mM NaCl in Buffer A. Eighty fractions of 0.5 ml each were collected. Column fractions were analyzed on a 15% SDS polyacrylamide gel and those containing Pol III* were pooled (fractions 32–50), concentrated by Centricon 30 to 230 µl and loaded onto a 24 ml Superose 6 column equilibrated in Buffer A containing 0.1 M NaCl. Fractions of 200 µl were collected and analyzed on a 15% SDS polyacrylamide gel. Fractions containing Pol III* were pooled (total protein, 760 µg in 2 ml) and stored at −70° C. Assuming a mass of 670 kDa for Pol III*, if all the τ had been incorporated there would have been 2.39 mg of Pol III*. Hence the recovery by this procedure is approximately 32%. Two other preparations of Pol III* were assembled by this same general method, with the following exceptions: the χΨ were placed only on γ by using pure γχΨ, and τ was not incubated with χΨ. In the other variation, χΨ was placed only on τ by using pure τχΨ (prepared similarly to γχΨ), and γ was not incubated with χΨ.

Method 2—In a volume of 3 ml were mixed 6.6 mg (52.5 nmol) γχΨ complex with 3.89 mg (105 nmol) δ', followed by incubation for 30 min. The mixture was chromatographed on a Mono Q HR 5/5 column equilibrated in Buffer A and eluted with a 32 ml linear gradient of 0–0.4 M NaCl in Buffer A. Fractions 40–43 were pooled to yield 4.2 mg γχΨδ' complex. The τ subunit (0.19 mg, 1.34 nmol) was mixed with 0.8 mg γδ'χΨ complex in 1.6 ml for 60 min followed by addition of 0.36 mg (9.33 nmol) δ in a final volume of 2.75 ml and incubated a further 30 min. During this time the core was constituted upon incubating α (0.516 mg, 4 nmol), ε (162 µg, 6 nmol), and θ (77 µg, 8.95 nmol) in 183 µml for 30 min. The core was mixed with the γδ'χΨτδ mixture and incubated 60 min.

Figure 8A:
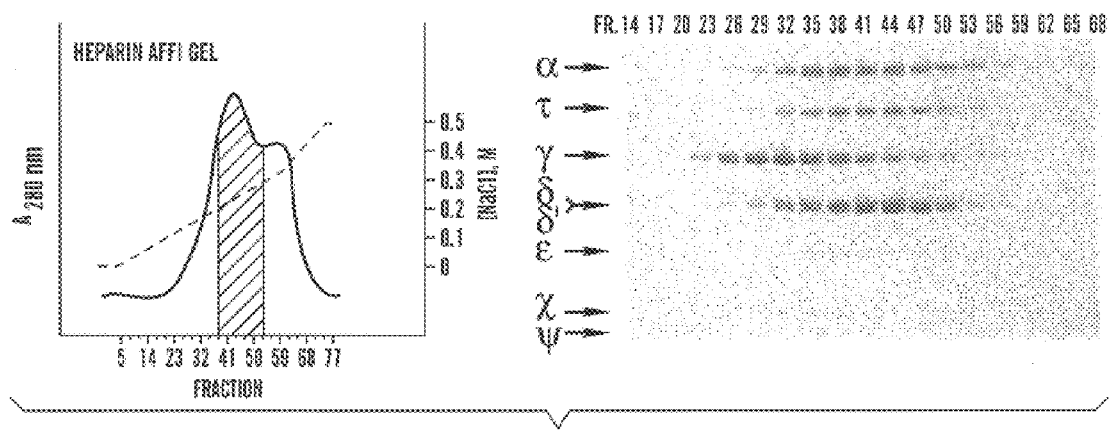
FIG. 8 illustrates the chromatographic purification of reconstituted Pol III*.
Figure 8B:
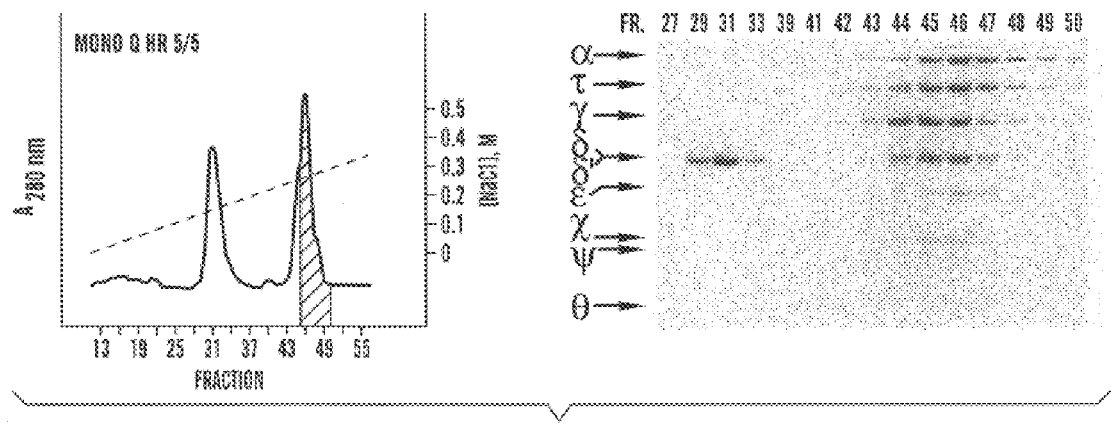
Figure 8C:
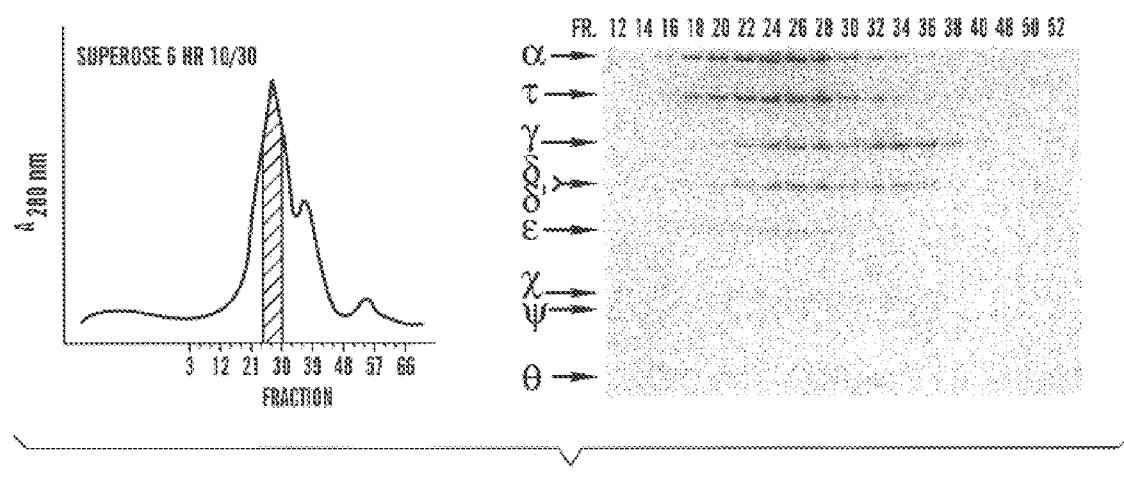

After all the subunit additions, Pol III* can be purified from the excess subunits and small subassemblies, as shown in FIG. 8. The mixture containing Pol III* was loaded onto a 2 ml Heparin Affi Gel column (BioRad) equilibrated with Buffer B and eluted with a 30 ml linear gradient of 0–0.325 M NaCl in Buffer B. Fractions of 0.5 ml were collected and analyzed on a SDS-PAGE for Pol III* and γ complex. Panel A of FIG. 8 shows the profile of elution from a Heparin column, which partially resolves excess γ complex (fractions 23–38) from Pol III* (fractions 32–54). Fractions 38–54 were pooled (resulting in some loss of Pol III* accompanying the removal of the bulk of excess γ complex) and loaded onto a Mono Q HR 5/5 column and then eluted as described for the γδ'χΨ complex. Excess δ and δ' coelute with Pol III* on the Heparin column but are cleanly separated from Pol III* by chromatography on a Mono Q column. Fractions were analyzed for Pol III* on a 15% SDS polyacrylamide gel (FIG. 8, Panel B). Fractions 45–50 were pooled, concentrated to 200 µl using a Centricon 30, and gel filtered on a 24 ml Superose 6 column in Buffer A containing 100 mM NaCl to remove the remaining γ complex (FIG. 8, Panel C). Fractions of 190 µl were collected and analyzed by SDS-PAGE. The persistent γ complex contaminant (fractions 32–38) now resolves from Pol III* (fractions 22–28), and the γ-less Pol III* contaminant becomes apparent (fractions 16–20). The γ-less Pol III* has a very high molecular weight and elutes earlier than Pol III*. To remove γ-less Pol III* and γ complex from the preparation, a narrow range of fractions, 25–30, was pooled (41 µg Pol III*) and stored at −70° C. Recovery by this procedure is approximately 5%. In another preparation, Pol III* was assembled by this method using τχΨδ' complex instead of γχΨδ', and adding γ later.

EXAMPLE 13

Characterization of Reconstituted pol III* Subassembly

Figure 9A:
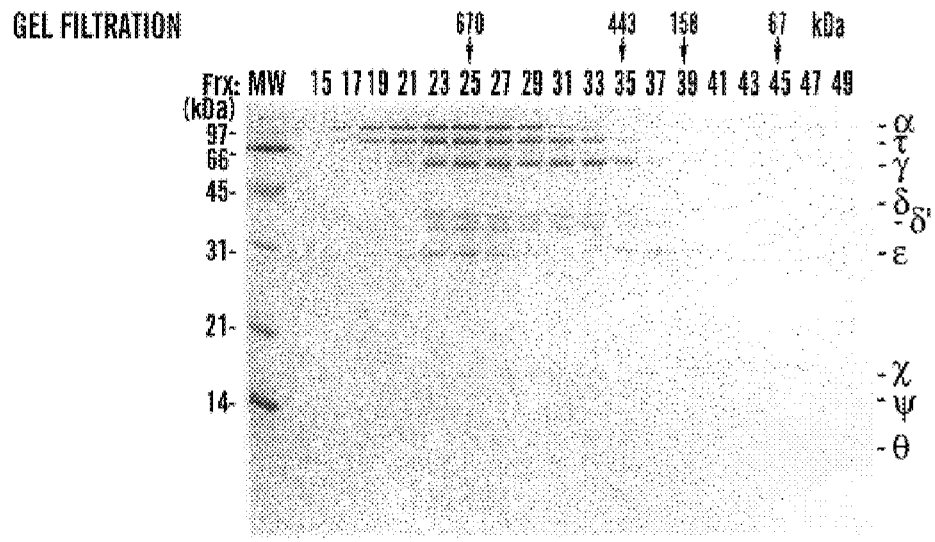
FIG. 9 illustrates a procedure for the determination of the size of reconstituted Pol III*.
Figure 9B:
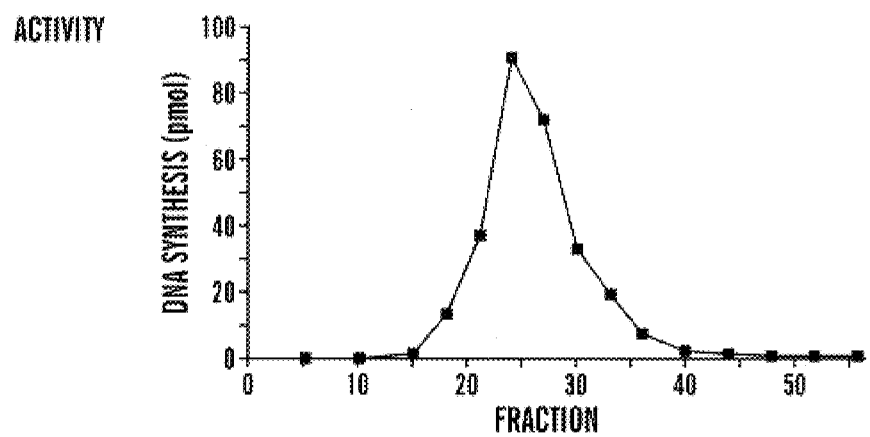
Figure 9C:
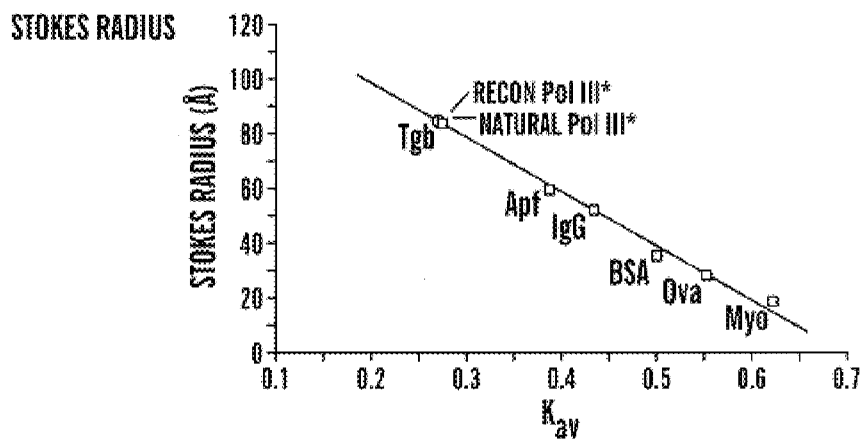

The size of reconstituted Pol III* was estimated by gel filtration analysis and comparison to size standards in FIG. 9, which yielded a Stokes radius of 85Å for an approximate mass of 670 kDa (see Table II). The mass of the natural Pol III* purified from E. coli without protein overproduction was also analyzed by gel filtration (FIG. 9, Panel C). It eluted in the same position as the reconstituted Pol III*, consistent with a previous study estimating the mass of purified natural Pol III* at 800 kDa (Maki et al., 1988, J. Biol. Chem., vol. 263, pp 6570–6578, the disclosures of which are incorporated herein by reference).

Figure 10A:
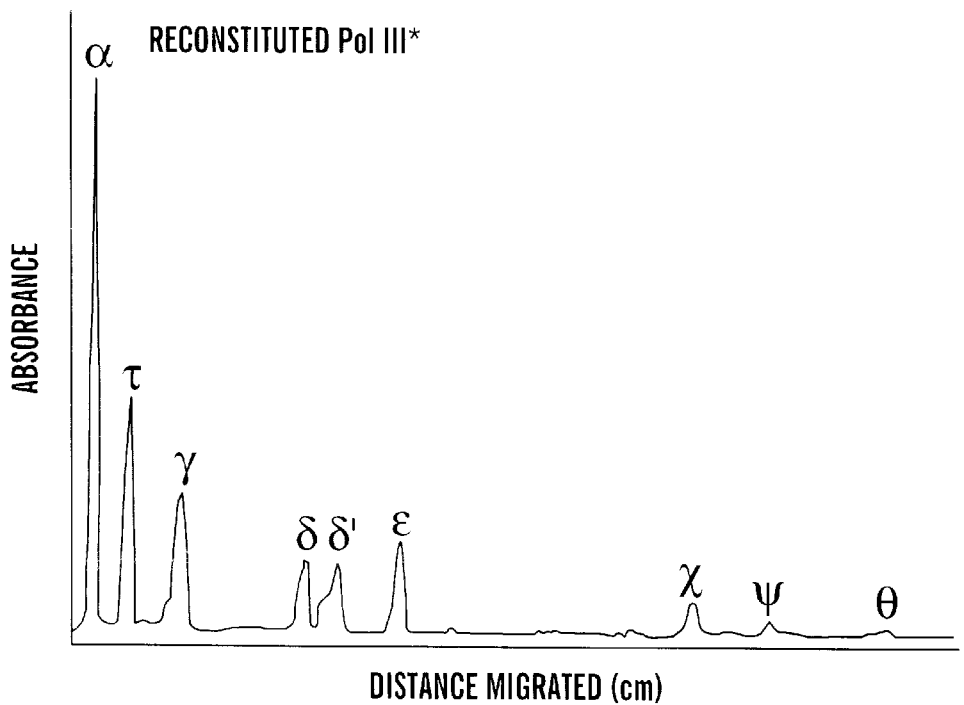
FIG. 10 compares the molar ratios of subunits in reconstituted and natural Pol III* determined by densitometric measurements on a gel filtration plate.
Figure 10B:
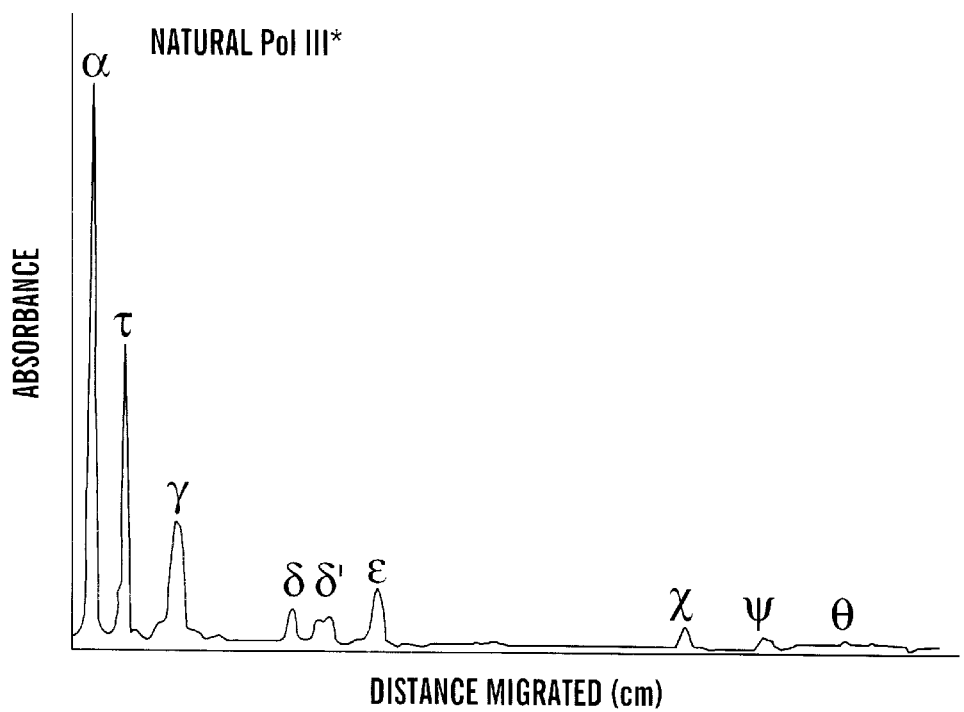

An attempt was made to determine the molar ratio of subunits in Pol III* by the HPLC technique, but a gradient that resolved all the subunits could not be found. Hence, the molar ratio of subunits in reconstituted Pol III* and naturally purified Pol III* was estimated by laser densitometry of a Coomassie Blue stained SDS polyacrylamide gel, whereby the differences in staining for each subunit were corrected by comparison to individual subunits of known concentration (from their extinction coefficients at 280 nm) analyzed in the same gel (FIG. 10). The scan of the Pol III* reconstituted by Method 1 (Panel A) is similar to that of the purified natural Pol III* (Panel B). The quantitation of the analysis is shown in Table 1. Each value obtained is an average of three lanes scanned and normalized to the value of τ; the error represents on standard deviation.

Table I. Subunit stoichiometry of purified Pol III*, reconstituted Pol III* and reconstituted "γ-less Pol III*".

TABLE I

Subunit stoichiometry of purified Pol III*, reconstituted Pol III* and reconstituted "γ-less Pol III*".

| Subunits Pol III* | Reconstituted Pol III* | Purified Natural Pol III* | Reconstituted γ-less Pol III* |
|---|---|---|---|
| α | 1.50 ± 0.02 | 1.90 ± 0.10 | 3.00 ± 0.33 |
| τ | (2.00) | (2.00) | (4.00) |
| γ | 2.74 ± 0.36 | 2.20 ± 0.10 | — |
| δ | 0.94 ± 0.16 | 0.62 ± 0.20 | 0.72 ± 0.10 |
| δ' | 0.98 ± 0.16 | 0.66 ± 0.14 | 0.68 ± 0.12 |
| ε | 1.76 ± 0.24 | 1.74 ± 0.70 | 2.72 ± 0.06 |
| χ | 0.70 ± 0.12 | 0.88 ± 0.34 | 0.52 ± 0.18 |
| Ψ | 0.74 ± 0.12 | 1.12 ± 0.52 | 1.00 ± 0.32 |
| θ[a] | ND | ND | ND |

[a] The stoichiometry of the θ subunit was not determined

The ratio of the α, ε, and τ subunits was approximately equimolar for both reconstituted and *E. coli* purified Pol III*. The intensity of the θ subunit was too weak to be determined accurately in this instance, but the εθ complex is 1:1, and thus it may be assumed that θ is equimolar to ε (Studwell-Vaughn and O'Donnell, 1993, *J. Biol. Chem.*, vol. 268, pp 11785–11791, the disclosures of which are incorporated herein by reference). The γ subunit in both the reconstituted and *E. coli* purified Pol III* is also approximately equimolar to α, ε and τ. However, even though the δ, δ', χ and Ψ subunits were added in excess during the assembly of Pol III*, these subunits are present at a level of approximately half that of the α, ε, τ and γ subunits in both the reconstituted and *E. coli* purified Pol III*.

The results for both reconstituted and purified natural Pol III* are most consistent with a dimer of γ and τ, two each of the core subunits (αεθ), and only one each of the δ, δ', χ and Ψ subunits. The single copy nature of δ and δ' can be seen by simple inspection of the scans in FIG. 10, the peak height of the double copy ε subunit (mw 28 kDa) being greater than the heights of the larger molecular weight but single copy δ (38.7 kDa) and δ' (37.0 kDa) subunits. This result is also consistent with previous studies on the composition of Pol III', which showed it to be composed of two of each subunit (McHenry, 1982, *J. Biol. Chem.*, vol. 257, pp 2657–2663; Studwell-Vaughn and O'Donnell, 1991, *J. Biol. Chem.*, vol. 266, pp 19833–19841, the disclosures of which are incorporated herein by reference). Although an earlier study of purified natural Pol III* suggested there were two of each subunit, analysis of the holoenzyme in that same study gave the following (after setting τ to two): $\alpha_2\tau_2\gamma_{2.56}\delta_{1.24}\delta'_{1.24}\varepsilon_{2.02}\chi_{1.14}\Psi_{0.90}\theta_{1.24}\beta_{4.28}$ (Maki et al., 1988, *J. Biol. Chem.* vol. 263, pp 6570–6578, the disclosures of which are incorporated herein by reference), quite consistent with the subunit ratios obtained here. The subunit stoichiometry predicts the molecular weight for Pol III* to be 673 kDa, as summarized in Table II, which is consistent with the size estimated by gel filtration. The molecular weights of the subunits were determined from the gene sequences.

TABLE II

Average subunit stoichiometry and calculated mass of Pol III*.

| Subunits | Molecular weight (kDa) | Ratio of subunits within Pol III* | Calculated Mass (kDa) |
|---|---|---|---|
| α | 129 | 2 | 258 |
| τ | 71 | 2 | 142 |
| γ | 47 | 2 | 94 |
| δ | 38.7 | 1 | 38.7 |
| δ' | 37 | 1 | 37 |
| ε | 27 | 2 | 54 |
| χ | 16.6 | 1 | 16.6 |
| Ψ | 15.2 | 1 | 15.2 |
| θ | 8.6 | 2 | 17.2 |
| | | Total Mass = | 672.7 |

Figure 11:
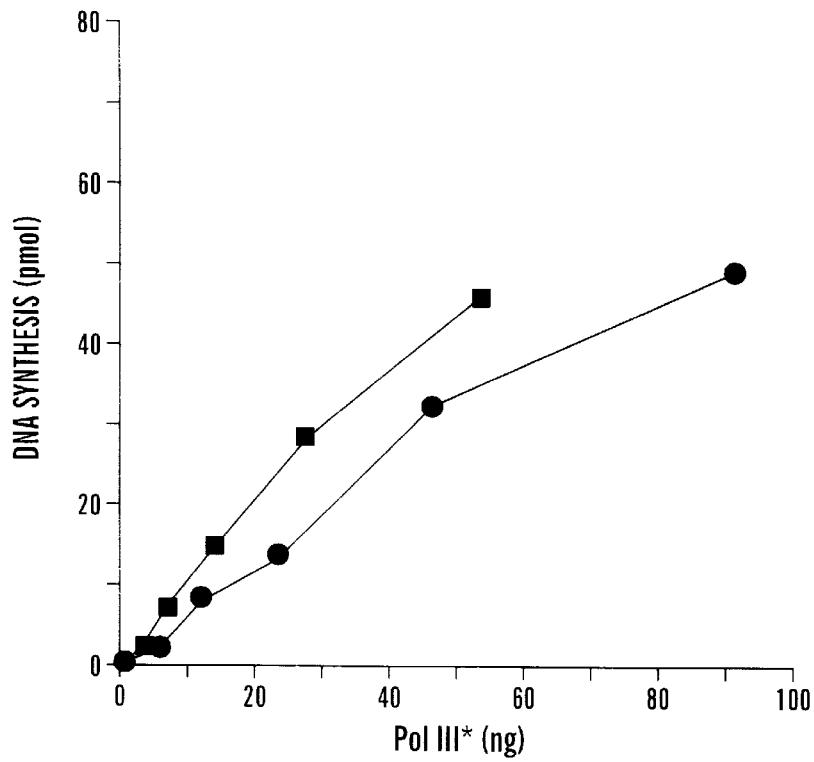
FIG. 11 is a graph comparing replication activity of reconstituted and purified natural Pol III*.

The activity of reconstituted Pol III* in the β-dependent replication of singly primed M13mp18 ssDNA coated with SSB was compared to that of purified natural Pol III*. The result, in FIG. 11, shows that the reconstituted Pol III* is 1.5-fold more active than purified natural Pol III*; their specific activities were $3.4 \times 10^6$ and $2.3 \times 10^6$ pmol incorporation/mg protein/minute, respectively. The similarity of the reconstituted Pol III* and purified natural Pol III* in size, subunit stoichiometry and replication activity indicates the reconstituted Pol III* is authentic.

Figure 12:
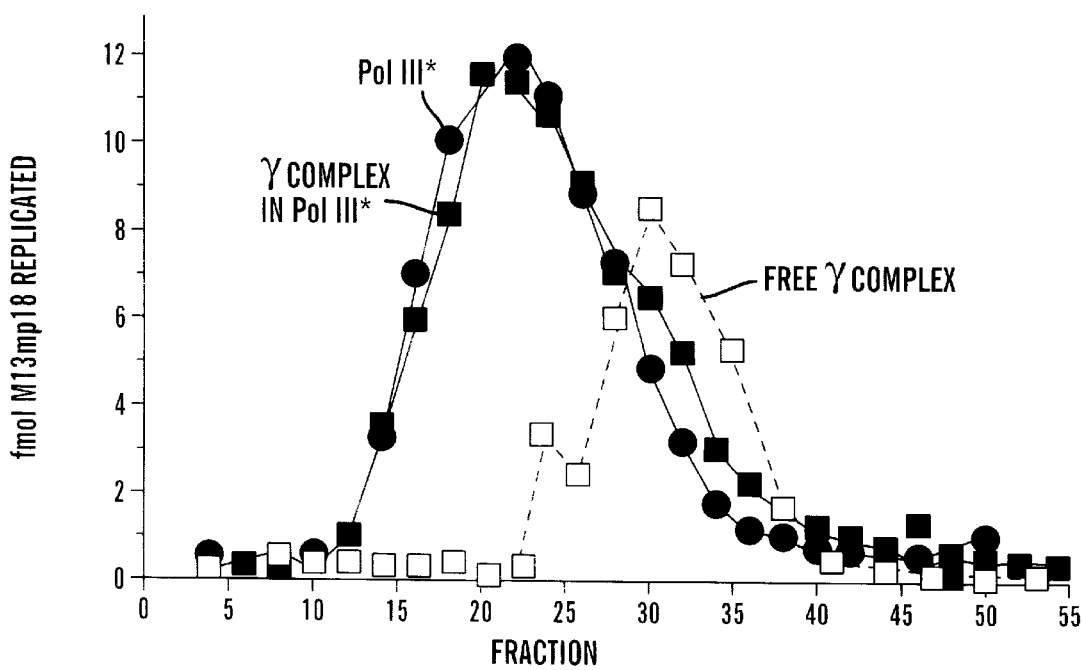
FIG. 12 depicts a gel filtration analysis to assess the stability of Pol III*.

In the cell there are 10–20 molecules of Pol III*, corresponding to a concentration of 17–34 nM (Kornberg and Baker, 1992, *DNA Replication* 2nd ed., W. H. Freeman and Co. New York, pp 165–194, the disclosures of which are incorporated herein by reference). FIG. 12 shows the results of a test of the ability of the Pol III* assembly to hold together at a concentration similar to that in the cell. At 30 nM Pol III*, the subunits cannot be followed by Coomassie staining (or silver staining) of a SDS polyacrylamide gel. Hence, Pol III* was identified in column fractions by assaying for replication of singly primed M13mp18 SSB coated ssDNA. If Pol III* falls apart, the γ complex should elute much later. Hence, the column fractions were also assayed for the γ complex. The result showed that Pol III* and γ complex activities corrugated in fractions 16–28, consistent with the size of Pol III*, and therefore the particle remains associated during gel filtration at these dilute conditions. As a control, a second gel filtration analysis using 30 nM γ complex shows the elution position of γ complex had it dissociated from Pol III* (dashed line in FIG. 12).

EXAMPLE 14

Radioactive Labeling of Proteins and Reconstitution of $^3$H-Pol III*

Subunits were tritiated by reductive methylation as described .(Kelman et al., 1994). The specific activities were: $^3$H-θ, 15,000 cpm/pmol; $^3$H-τ, 29,000 cpm/pmol; $^3$H-γ, 29,000 cpm/pmol, and $^3$H-β, 67,000 cpm/pmol. The $^3$H-β retained 100% activity with Pol III*; the activity of the other $^3$H-subunits was within 90% of the unlabeled subunit as determined by constituting them into the 9-subunit Pol III* (described below), followed by assaying replication activity with β, as described in Maki et al., 1988, *J. Biol. Chem.*, vol. 263, pp 6570–6578, the disclosures of which are incorporated herein by reference.

Pol III* was assembled in stages by incubating 352 mg γ (3.7 nmol as dimer) with 178 mg τ (1.25 muol as dimer), 145 mg χ (8.73 nmol), 114 mg Ψ (7.5 nmol) in 789 ml buffer A for 30 minutes at 15° C. To this was added 328 mg δ (8.48 nmol) and 278 mg δ' (7.53 nmol) in 1394 ml buffer A, followed by further incubation for 30 minutes at 15° C. During this time pol III core was constituted in a separate tube containing 200 mg $\alpha$ (1.55 nmol as monomer), 154 mg $\epsilon$ (5.6 nmol as monomer) and 76 mg $\theta$ (8.84 nmol as monomer) in 283 ml buffer A, which was incubated 30 minutes at 15° C. Then the contents of the two tubes were mixed, and the resulting mixture was incubated for 30 minutes at 15° C. Pol III* was separated from all free subunits except $\delta$ and $\delta'$ on a 1 ml Heparin Agarose column eluted with a 15 ml gradient of 0–325 mM NaCl in buffer A. Fractions containing Pol III* were pooled, dialyzed and then chromatographed on a 1 ml Mono Q column eluted with a 19 ml gradient of 0–0.4 M NaCl in buffer A, which cleanly resolved Pol III* from $\delta$ and $\delta'$. Pol III* was dialyzed against buffer A before storage at −70° C.

$\beta^{PK}$, a derivative of $\beta$ that contain an additional six amino acids at the C-terminus, was constructed. The $\beta^{PK}$ is an efficient substrate for cAMP dependent protein kinase and was labeled using [$\gamma$-$^{32}$P]-ATP to a specific activity of 20,000–65,000 cmp/pmol as described (Kelman et al., 1994). The $\beta^{PK}$ and $^{32}$P-labeled $\beta^{PK}$ were as active as wild type $\beta$ in replication of primed ssDNA using Pol III*.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A process for reconstituting the $\gamma$-less Pol III* subassembly from *E. coli* from subunits $\tau$, $\alpha$, $\epsilon$, $\theta$, $\delta$, $\delta'$, $\chi$, and $\Psi$, which comprises:
    combining $\tau$, $\alpha$, $\epsilon$, $\theta$, $\delta$, $\delta'$, $\chi$, and $\Psi$, under conditions effective to form said $\gamma$-less Pol III* subassembly, wherein said combining comprises:
      combining $\chi$, $\Psi$, $\delta$, and $\delta'$ under conditions effective to form a $\chi\Psi\delta\delta'$ complex;
      combining said $\chi\Psi\delta\delta'$ complex with $\tau$ under conditions effective to form a $\tau\chi\Psi\delta\delta'$ complex;
      combining said $\tau\chi\Psi\delta\delta'$ complex with $\alpha$, $\epsilon$, $\theta$; and
      recovering said $\gamma$-less Pol III* subassembly.

2. A process for reconstituting an $\alpha\tau\chi\Psi\delta\delta'$ subassembly from *E. coli* from subunits $\tau$, $\alpha$, $\delta$, $\delta'$, $\chi$, and $\Psi$, which comprises:
    combining $\tau$, $\alpha$, $\delta$,$\delta'$, $\chi$, and $\Psi$ in any order under conditions effective to form said $\alpha\tau\chi\Psi\delta\delta'$ subassembly and
    recovering said $\alpha\tau\chi\Psi\delta\delta'$ subassembly.

3. A process of claim 2, wherein said combining comprises:
    combining $\tau$, $\chi$, $\Psi$, $\delta$, and $\delta'$ under conditions effective to form a $\tau\chi\Psi\delta\delta'$ complex; and
    combining said $\tau\chi\Psi\delta\delta'$ complex with $\alpha$ to form said $\alpha\tau\chi\Psi\delta\delta'$ subassembly.

4. A process for reconstituting an $\alpha\tau\delta\delta'$ subassembly from *E. coli* from $\tau$, $\alpha$, $\delta$, and $\delta'$, which comprises:
    combining $\tau$, $\alpha$, $\delta$, and $\delta'$ in any order under conditions effective to form said $\alpha\tau\delta\delta'$ subassembly and
    recovering said $\alpha\tau\delta\delta'$ subassembly.

5. A process of claim 4, wherein said combining further comprises:
    combining $\tau$, $\delta$, and $\delta'$ under conditions effective to form a $\tau\delta\delta'$ complex; and
    combining said $\tau\delta\delta'$ complex with $\alpha$ under conditions effective to form said $\alpha\tau\delta\delta'$ subassembly.

6. A process for reconstituting an $\alpha\epsilon\theta\tau\delta\delta'$ subassembly from *E. coli* from subunits $\tau$, $\alpha$, $\epsilon$, $\theta$, $\delta$, and $\delta'$, which comprises:
    combining $\tau$, $\alpha$, $\epsilon$, $\theta$, $\delta$, and $\delta'$ in any order under conditions effective to form said $\alpha\epsilon\theta\tau\delta\delta'$ subassembly and
    recovering said $\alpha\epsilon\theta\tau\delta\delta'$ subassembly.

7. A process of claim 6, wherein said combining further comprises:
    combining $\tau$, $\delta$, and $\delta'$ under conditions effective to form a $\tau\delta\delta'$ complex; and
    combining said $\tau\delta\delta'$ with $\alpha$, $\epsilon$, and $\theta$ under conditions effective to form said $\alpha\epsilon\theta\tau\delta\delta'$ complex.

* * * * *

UNITED STATES PATENT AND TRADEMARK OFFICE
CERTIFICATE OF CORRECTION

| | |
|---|---|
| PATENT NO. | : 6,221,642 B1 |
| APPLICATION NO. | : 09/282917 |
| DATED | : April 24, 2001 |
| INVENTOR(S) | : Michael E. O'Donnell |

It is certified that error appears in the above-identified patent and that said Letters Patent is hereby corrected as shown below:

Col. 1 at lines 12-14, delete "This work was supported by grants from the National Institutes of Health (GM38839) and the National Science Foundation (MCB-9303921)." and insert --This invention was made with government support under grant GM38839 awarded by National Institutes of Health and grant MCB-9303921 awarded by National Science Foundation. The government has certain rights in the invention-- in its place.

Signed and Sealed this

Sixteenth Day of December, 2008

JON W. DUDAS
*Director of the United States Patent and Trademark Office*